United States Patent
Leung et al.

(10) Patent No.: US 9,932,397 B2
(45) Date of Patent: Apr. 3, 2018

(54) VEGFA/ANG2 COMPOUNDS

(71) Applicant: Eli Lilly and Company, Indianapolis, IN (US)

(72) Inventors: Donmienne Doen Mun Leung, San Diego, CA (US); Ying Tang, San Diego, CA (US); Peter Edward Vaillancourt, Del Mar, CA (US); Jianghuai Xu, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 139 days.

(21) Appl. No.: 15/005,042

(22) Filed: Jan. 25, 2016

(65) Prior Publication Data
US 2016/0215045 A1   Jul. 28, 2016

Related U.S. Application Data

(60) Provisional application No. 62/108,600, filed on Jan. 28, 2015.

(51) Int. Cl.
*C07K 16/22* (2006.01)
*A61K 39/395* (2006.01)
*A61K 39/00* (2006.01)

(52) U.S. Cl.
CPC .......... *C07K 16/22* (2013.01); *A61K 39/3955* (2013.01); *A61K 2039/505* (2013.01); *A61K 2039/507* (2013.01); *C07K 2317/14* (2013.01); *C07K 2317/31* (2013.01); *C07K 2317/35* (2013.01); *C07K 2317/56* (2013.01); *C07K 2317/622* (2013.01); *C07K 2317/73* (2013.01); *C07K 2317/76* (2013.01); *C07K 2317/92* (2013.01); *C07K 2319/00* (2013.01)

(58) Field of Classification Search
None
See application file for complete search history.

(56) References Cited

FOREIGN PATENT DOCUMENTS

| WO | 2000/64946 A2 | 11/2000 |
|---|---|---|
| WO | 2007/068895 A1 | 6/2007 |
| WO | 2010/040508 A1 | 4/2010 |
| WO | 2010/145793 A1 | 12/2010 |
| WO | 2011/117329 A1 | 9/2011 |
| WO | 2011/117330 A1 | 9/2011 |
| WO | 2012/009705 A1 | 1/2012 |
| WO | 2012/131078 A1 | 10/2012 |
| WO | 2014/137961 A1 | 9/2014 |
| WO | 2015/179168 A1 | 11/2015 |

OTHER PUBLICATIONS

Kienast et al. (Clinical Cancer Research, 19(24), pp. 6730-6740, Dec. 15, 2013) (Year: 2013).*
Brown, J. et al., "A Human Monoclonal Anti-ANG2 Antibody Leads to Broad Antitumor Activity in Combination with VEGF Inhibitors and Chemotherapy Agents in Preclinical Models," Molecular Cancer Therapeutics; 9(1), pp. 145-156 (Jan. 2010).
Leow, C. et al., "MEDI3617, a human anti-Angiopoietin 2 monoclonal antibody, inhibits angiogenesis and tumor growth in human tumor xenograft models," International Journal of Oncology; v.40, pp. 1321-1330 (2012).
Koh, Y. et al., "Double Antiangiogenic Protein, DAAP, Targeting VEGF-A and Angiopoietins in Tumor Angiogenesis, Metastasis, and Vascular Leakage," Cancer Cell; v.18, pp. 171-184 (Aug. 17, 2010).
Kienast, Y. et al., "Ang-2-VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy," Clinical Cancer Research; 19(24), pp. 6730-6740 (Dec. 15, 2013).
Huang, H. et al., "Specifically Targeting Angiopoietin-2 Inhibits Angiogenesis, Tie2-Expressing Monocyte Infiltration, and Tumor Growth," Clinical Cancer Research; 17(5), pp. 1001-1011 (Mar. 1, 2011).
Hashizume, H. et al., "Complementary Actions of Inhibitors of Angiopoietin-2 and VEGF on Tumor Angiogenesis and Growth," Cancer Research; 70(6), pp. 2213-2773 (Mar. 2, 2010).
Daly, C. et al., "Angiopoietin-2 Functions as a Tie2 Agonist in Tumor Models, Where It Limits the Effects of VEGF Inhibition," Cancer Research; 73(1), pp. 108-118 (Jan. 1, 2013).
Coxon, A. et al., "Context-Dependent Role of Angiopoietin-1 Inhibition in the Suppression of Angiogenesis and Tumor Growth: Implications for AMG 386, an Angiopoietin-1/2—Neutralizing Peptibody," Molecular Cancer Therapeutics; 9 (10), pp. 2641-2651 (Oct. 2010).

* cited by examiner

*Primary Examiner* — Laura B Goddard
*Assistant Examiner* — Meera Natarajan
(74) *Attorney, Agent, or Firm* — Robert Brian Johnson

(57) ABSTRACT

The present invention relates to compounds that bind to human vascular endothelial growth factor A (VEGFA) and human angiopoietin-2 (Ang2), and may be useful for treating angiogenic eye diseases, such as diabetic and other proliferative retinopathies, and for cancer, especially solid tumors driven by VEGFA and Ang2, including gastric, lung, hepatocellular carcinoma, ovarian, colorectal, and breast cancers.

16 Claims, No Drawings

SEQUENCE LISTING

<160> NUMBER OF SEQ ID NOS: 17

<210> SEQ ID NO 1
<211> LENGTH: 123
<212> TYPE: PRT
<213> ORGANISM: Artificial Sequence
<220> FEATURE:
<223> OTHER INFORMATION: Synthetic Construct

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Asp Ser Ser Trp Tyr Phe Ala Phe Asp Ile
            100                 105                 110

Trp Gly Gln Gly Thr Thr Val Thr Val Ser Ser
        115                 120
```

<210> SEQ ID NO 2
<211> LENGTH: 449
<212> TYPE: PRT
<213> ORGANISM: Artificial Sequence
<220> FEATURE:
<223> OTHER INFORMATION: Synthetic Construct

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Asp Ser Ser Trp Tyr Phe Ala Phe Asp Ile
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly

<210> SEQ ID NO 3
<211> LENGTH: 716
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95
Ala Arg Asp Pro Ser Asp Ser Ser Trp Tyr Phe Ala Phe Asp Ile
            100                 105                 110
Trp Gly Gln Gly Thr Thr Val Thr Val Ser Ser Ala Ser Thr Lys Gly
            115                 120                 125
Pro Ser Val Phe Pro Leu Ala Pro Cys Ser Arg Ser Thr Ser Glu Ser
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Lys Thr Tyr Thr Cys Asn Val
            195                 200                 205
Asp His Lys Pro Ser Asn Thr Lys Val Asp Lys Arg Val Glu Ser Lys
    210                 215                 220
Tyr Gly Pro Pro Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Glu Met Thr Lys Asn Gln Val Ser Leu
            355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
            435                 440                 445
Gly Gly Gly Gly Ser Gly Gly Gly Ser Gly Gly Gly Gly Ser Gln
    450                 455                 460
Val Gln Leu Val Gln Ser Gly Ala Glu Val Lys Lys Pro Gly Ala Ser
465                 470                 475                 480
Val Lys Val Ser Cys Lys Ala Ser Gly Tyr Ser Phe Thr Asp Tyr Asn
                485                 490                 495
Met Val Trp Val Arg Gln Ala Pro Gly Gln Cys Leu Glu Trp Met Gly
            500                 505                 510
```

Tyr Ile Asp Pro Tyr Asn Gly Gly Thr Gly Tyr Asn Gln Lys Phe Glu
            515                 520                 525

Gly Arg Val Thr Met Thr Thr Asp Thr Ser Thr Ser Thr Ala Tyr Met
        530                 535                 540

Glu Leu Arg Ser Leu Arg Ser Asp Asp Thr Ala Val Tyr Tyr Cys Ala
545                 550                 555                 560

Arg Thr Arg Asp Arg Tyr Asp Val Trp Tyr Phe Asp Val Trp Gly Gln
                565                 570                 575

Gly Thr Leu Val Thr Val Ser Ser Gly Gly Gly Ser Gly Gly Gly
            580                 585                 590

Gly Ser Gly Gly Gly Ser Gly Gly Gly Ser Gly Gly Gly Gly
            595                 600                 605

Ser Asp Ile Gln Met Thr Gln Ser Pro Ser Ser Val Ser Ala Ser Val
            610                 615                 620

Gly Asp Arg Val Thr Ile Thr Cys Lys Ala Ser Gln Asp Val Tyr Ile
625                 630                 635                 640

Ala Val Ala Trp Tyr Gln Gln Lys Pro Gly Lys Ala Pro Lys Leu Leu
                645                 650                 655

Ile Tyr Trp Ala Ser Thr Arg Asp Thr Gly Val Pro Ser Arg Phe Ser
                660                 665                 670

Gly Ser Gly Ser Gly Thr Asp Phe Thr Leu Thr Ile Ser Ser Leu Gln
            675                 680                 685

Pro Glu Asp Phe Ala Thr Tyr Tyr Cys His Gln Tyr Ser Ser Tyr Pro
            690                 695                 700

Pro Thr Phe Gly Cys Gly Thr Lys Val Glu Ile Lys
705                 710                 715

<210> SEQ ID NO 4
<211> LENGTH: 107
<212> TYPE: PRT
<213> ORGANISM: Artificial Sequence
<220> FEATURE:
<223> OTHER INFORMATION: Synthetic Construct

<400> SEQUENCE: 4

Asp Ile Val Met Thr Gln Ser Pro Ala Thr Leu Ser Val Ser Pro Gly
1               5                   10                  15

Gln Arg Ala Thr Leu Ser Cys Arg Ala Ser Gln Asn Ile Arg Asn Asn
            20                  25                  30

Leu Ala Trp Tyr Gln Gln Lys Arg Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Ala Asp Phe Thr Leu Thr Ile Ser Lys Leu Glu Pro
65                  70                  75                  80

Glu Asp Phe Ala Val Tyr Tyr Cys Gln Gln Tyr Gly Ser Ser Pro Arg
                85                  90                  95

Thr Phe Gly Gln Gly Thr Lys Val Asp Ile Lys
            100                 105

<210> SEQ ID NO 5
<211> LENGTH: 214
<212> TYPE: PRT
<213> ORGANISM: Artificial Sequence
<220> FEATURE:
<223> OTHER INFORMATION: Synthetic Construct

<400> SEQUENCE: 5

Asp Ile Val Met Thr Gln Ser Pro Ala Thr Leu Ser Val Ser Pro Gly
1               5                   10                  15

Gln Arg Ala Thr Leu Ser Cys Arg Ala Ser Gln Asn Ile Arg Asn Asn
            20                  25                  30

Leu Ala Trp Tyr Gln Gln Lys Arg Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Ala Asp Phe Thr Leu Thr Ile Ser Lys Leu Glu Pro
65                  70                  75                  80

Glu Asp Phe Ala Val Tyr Tyr Cys Gln Gln Tyr Gly Ser Ser Pro Arg
                85                  90                  95

Thr Phe Gly Gln Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 253
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Val Trp Val Arg Gln Ala Pro Gly Gln Cys Leu Glu Trp Met
        35                  40                  45

Gly Tyr Ile Asp Pro Tyr Asn Gly Gly Thr Gly Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Arg Asp Arg Tyr Asp Val Trp Tyr Phe Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gly Gly Gly Ser Gly Gly Gly

```
                130              135              140
Gly Ser Asp Ile Gln Met Thr Gln Ser Pro Ser Ser Val Ser Ala Ser
145                 150                 155                 160

Val Gly Asp Arg Val Thr Ile Thr Cys Lys Ala Ser Gln Asp Val Tyr
                165                 170                 175

Ile Ala Val Ala Trp Tyr Gln Gln Lys Pro Gly Lys Ala Pro Lys Leu
            180                 185                 190

Leu Ile Tyr Trp Ala Ser Thr Arg Asp Thr Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys His Gln Tyr Ser Ser Tyr
225                 230                 235                 240

Pro Pro Thr Phe Gly Cys Gly Thr Lys Val Glu Ile Lys
                245                 250
```

<210> SEQ ID NO 7
<211> LENGTH: 121
<212> TYPE: PRT
<213> ORGANISM: Artificial Sequence
<220> FEATURE:
<223> OTHER INFORMATION: Synthetic Construct

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Val Trp Val Arg Gln Ala Pro Gly Gln Cys Leu Glu Trp Met
        35                  40                  45

Gly Tyr Ile Asp Pro Tyr Asn Gly Gly Thr Gly Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Arg Asp Arg Tyr Asp Val Trp Tyr Phe Asp Val Trp Gly
            100                 105                 110

Gln Gly Thr Leu Val Thr Val Ser Ser
        115                 120
```

<210> SEQ ID NO 8
<211> LENGTH: 107
<212> TYPE: PRT
<213> ORGANISM: Artificial Sequence
<220> FEATURE:
<223> OTHER INFORMATION: Synthetic Construct

<400> SEQUENCE: 8

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Tyr Ile Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg Asp Thr Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Ser Ser Tyr Pro Pro
                 85                  90                  95

Thr Phe Gly Cys Gly Thr Lys Val Glu Ile Lys
            100                 105

<210> SEQ ID NO 9
<211> LENGTH: 2148
<212> TYPE: PRT
<213> ORGANISM: Artificial Sequence
<220> FEATURE:
<223> OTHER INFORMATION: Synthetic Construct

<400> SEQUENCE: 9

Gly Ala Gly Gly Thr Gly Cys Ala Gly Cys Thr Gly Thr Thr Gly Gly
 1               5                  10                  15

Ala Gly Thr Cys Thr Gly Gly Gly Gly Ala Gly Gly Cys Thr Thr Thr
                20                  25                  30

Gly Gly Thr Ala Cys Ala Gly Cys Cys Thr Gly Gly Gly Gly Gly Gly
                35                  40                  45

Thr Cys Cys Cys Thr Gly Ala Gly Ala Cys Thr Cys Thr Cys Cys Thr
 50                  55                  60

Gly Thr Gly Cys Ala Gly Cys Cys Thr Cys Thr Gly Gly Ala Thr Thr
 65                  70                  75                  80

Cys Ala Cys Cys Thr Thr Thr Ala Gly Cys Ala Gly Cys Thr Ala Thr
                 85                  90                  95

Gly Cys Cys Ala Thr Gly Ala Gly Cys Thr Gly Gly Gly Thr Cys Cys
                100                 105                 110

Gly Cys Cys Ala Gly Gly Cys Thr Cys Cys Ala Gly Gly Ala Ala Ala
                115                 120                 125

Gly Gly Gly Gly Cys Thr Gly Gly Ala Gly Thr Gly Gly Gly Thr Cys
                130                 135                 140

Thr Cys Ala Gly Cys Thr Ala Thr Thr Ala Gly Thr Gly Gly Thr Ala
145                 150                 155                 160

Gly Thr Gly Gly Thr Gly Gly Thr Ala Gly Cys Ala Cys Ala Thr Ala
                165                 170                 175

Cys Thr Ala Cys Gly Cys Ala Gly Ala Cys Thr Cys Cys Gly Thr Gly
                180                 185                 190

Ala Ala Gly Gly Gly Cys Cys Gly Gly Thr Thr Cys Ala Cys Cys Ala
                195                 200                 205

Thr Cys Thr Cys Cys Ala Gly Ala Gly Ala Cys Ala Ala Thr Thr Cys
                210                 215                 220

Cys Ala Ala Gly Ala Ala Cys Ala Cys Gly Cys Thr Gly Thr Ala Thr
225                 230                 235                 240

Cys Thr Gly Cys Ala Ala Ala Thr Gly Ala Ala Cys Ala Gly Cys Cys
                245                 250                 255

Thr Gly Ala Gly Ala Gly Cys Cys Gly Ala Gly Gly Ala Cys Ala Cys
                260                 265                 270

Gly Gly Cys Cys Gly Thr Ala Thr Ala Thr Thr Ala Cys Thr Gly Thr
                275                 280                 285

Gly Cys Ala Ala Gly Ala Gly Ala Thr Cys Cys Cys Thr Cys Gly Gly
                290                 295                 300

Ala Thr Ala Gly Cys Ala Gly Cys Ala Gly Cys Thr Gly Gly Thr Ala
305                 310                 315                 320
```

-continued

```
Cys Thr Thr Thr Gly Cys Thr Thr Thr Thr Gly Ala Thr Ala Thr Cys
                325                 330                 335

Thr Gly Gly Gly Gly Cys Cys Ala Ala Gly Gly Gly Ala Cys Cys Ala
            340                 345                 350

Cys Gly Gly Thr Cys Ala Cys Cys Gly Thr Cys Thr Cys Cys Thr Cys
        355                 360                 365

Ala Gly Cys Cys Thr Cys Thr Ala Cys Cys Ala Ala Gly Gly Gly Cys
    370                 375                 380

Cys Cys Ala Thr Cys Gly Gly Thr Cys Thr Thr Cys Cys Cys Gly Cys
385                 390                 395                 400

Thr Ala Gly Cys Gly Cys Cys Cys Thr Gly Cys Thr Cys Cys Ala Gly
                405                 410                 415

Gly Ala Gly Cys Ala Cys Cys Thr Cys Cys Gly Ala Gly Ala Gly Cys
            420                 425                 430

Ala Cys Ala Gly Cys Cys Gly Cys Cys Cys Thr Gly Gly Gly Cys Thr
        435                 440                 445

Gly Cys Cys Thr Gly Gly Thr Cys Ala Ala Gly Gly Ala Cys Thr Ala
    450                 455                 460

Cys Thr Thr Cys Cys Cys Cys Gly Ala Ala Cys Cys Gly Gly Thr Gly
465                 470                 475                 480

Ala Cys Gly Gly Thr Gly Thr Cys Gly Thr Gly Gly Ala Ala Cys Thr
                485                 490                 495

Cys Ala Gly Gly Cys Gly Cys Cys Cys Thr Gly Ala Cys Cys Ala Gly
            500                 505                 510

Cys Gly Gly Cys Gly Thr Gly Cys Ala Cys Ala Cys Cys Thr Thr Cys
        515                 520                 525

Cys Cys Gly Gly Cys Thr Gly Thr Cys Cys Thr Ala Cys Ala Gly Thr
    530                 535                 540

Cys Cys Thr Cys Ala Gly Gly Ala Cys Thr Cys Thr Ala Cys Thr Cys
545                 550                 555                 560

Cys Cys Thr Cys Ala Gly Cys Ala Gly Cys Gly Thr Gly Gly Thr Gly
                565                 570                 575

Ala Cys Cys Gly Thr Gly Cys Cys Cys Thr Cys Cys Ala Gly Cys Ala
            580                 585                 590

Gly Cys Thr Thr Gly Gly Gly Cys Ala Cys Gly Ala Ala Gly Ala Cys
        595                 600                 605

Cys Thr Ala Cys Ala Cys Cys Thr Gly Cys Ala Ala Cys Gly Thr Ala
    610                 615                 620

Gly Ala Thr Cys Ala Cys Ala Ala Gly Cys Cys Cys Ala Gly Cys Ala
625                 630                 635                 640

Ala Cys Ala Cys Cys Ala Ala Gly Gly Thr Gly Gly Ala Cys Ala Ala
                645                 650                 655

Gly Ala Gly Ala Gly Thr Thr Gly Ala Gly Thr Cys Cys Ala Ala Ala
            660                 665                 670

Thr Ala Thr Gly Gly Thr Cys Cys Cys Cys Cys Ala Thr Gly Cys Cys
        675                 680                 685

Cys Ala Cys Cys Cys Thr Gly Cys Cys Cys Ala Gly Cys Ala Cys Cys
    690                 695                 700

Thr Gly Ala Gly Gly Cys Cys Gly Cys Cys Gly Gly Gly Gly Gly Ala
705                 710                 715                 720

Cys Cys Ala Thr Cys Ala Gly Thr Cys Thr Thr Cys Cys Thr Gly Thr
                725                 730                 735

Thr Cys Cys Cys Cys Cys Cys Ala Ala Ala Ala Cys Cys Cys Ala Ala
```

-continued

Gly Gly Ala Cys Ala Cys Thr Cys Thr Cys Ala Thr Gly Ala Thr Cys
            740                 745                 750

Thr Cys Cys Cys Gly Gly Ala Cys Cys Cys Thr Gly Ala Gly Gly
    755                 760                 765

Thr Cys Ala Cys Gly Thr Gly Cys Gly Thr Gly Thr Gly Gly Thr
785                 790                 795                 800

Gly Gly Ala Cys Gly Thr Gly Ala Gly Cys Ala Gly Gly Ala Ala
                805                 810                 815

Gly Ala Cys Cys Cys Gly Ala Gly Gly Thr Cys Cys Ala Gly Thr
            820                 825                 830

Thr Cys Ala Ala Cys Thr Gly Gly Thr Ala Cys Gly Thr Gly Gly Ala
            835                 840                 845

Thr Gly Gly Cys Gly Thr Gly Gly Ala Gly Gly Thr Gly Cys Ala Thr
            850                 855                 860

Ala Ala Thr Gly Cys Cys Ala Ala Gly Ala Cys Ala Ala Gly Cys
865                 870                 875                 880

Cys Gly Cys Gly Gly Gly Ala Gly Gly Ala Gly Cys Ala Gly Thr Thr
                885                 890                 895

Cys Ala Ala Cys Ala Gly Cys Ala Cys Gly Thr Ala Cys Cys Gly Thr
            900                 905                 910

Gly Thr Gly Gly Thr Cys Ala Gly Cys Gly Thr Cys Cys Thr Cys Ala
            915                 920                 925

Cys Cys Gly Thr Cys Cys Thr Gly Cys Ala Cys Ala Gly Gly Ala
930                 935                 940

Cys Thr Gly Gly Cys Thr Gly Ala Ala Cys Gly Gly Cys Ala Ala Gly
945                 950                 955                 960

Gly Ala Gly Thr Ala Cys Ala Ala Gly Thr Gly Cys Ala Ala Gly Gly
                965                 970                 975

Thr Cys Thr Cys Cys Ala Ala Cys Ala Ala Ala Gly Gly Cys Cys Thr
            980                 985                 990

Cys Cys Cys Gly Thr Cys Cys Thr Cys Cys Ala Thr Cys Gly Ala Gly
            995                 1000                1005

Ala Ala Ala Ala Cys Cys Ala Thr Cys Thr Cys Cys Ala Ala Ala
    1010                1015                1020

Gly Cys Cys Ala Ala Ala Gly Gly Gly Cys Ala Gly Cys Cys Cys
    1025                1030                1035

Cys Gly Ala Gly Ala Gly Cys Cys Ala Cys Ala Gly Gly Thr Gly
    1040                1045                1050

Thr Ala Cys Ala Cys Cys Cys Thr Gly Cys Cys Cys Cys Cys Ala
    1055                1060                1065

Thr Cys Cys Cys Ala Gly Gly Ala Gly Gly Ala Gly Ala Thr Gly
    1070                1075                1080

Ala Cys Cys Ala Ala Gly Ala Ala Cys Cys Ala Gly Gly Thr Cys
    1085                1090                1095

Ala Gly Cys Cys Thr Gly Ala Cys Cys Thr Gly Cys Cys Thr Gly
    1100                1105                1110

Gly Thr Cys Ala Ala Ala Gly Gly Cys Thr Thr Cys Thr Ala Cys
    1115                1120                1125

Cys Cys Cys Ala Gly Cys Gly Ala Cys Ala Thr Cys Gly Cys Cys
    1130                1135                1140

Gly Thr Gly Gly Ala Gly Thr Gly Gly Gly Ala Ala Ala Gly Cys
    1145                1150                1155

```
Ala Ala Thr Gly Gly Gly Cys Ala Gly Cys Cys Gly Gly Ala Gly
    1160            1165                1170

Ala Ala Cys Ala Ala Cys Thr Ala Cys Ala Ala Gly Ala Cys Cys
    1175            1180                1185

Ala Cys Gly Cys Cys Thr Cys Cys Cys Gly Thr Gly Cys Thr Gly
    1190            1195                1200

Gly Ala Cys Thr Cys Gly Ala Cys Gly Gly Cys Thr Cys Cys
    1205            1210                1215

Thr Thr Cys Thr Thr Cys Thr Cys Thr Ala Cys Ala Gly Cys
    1220            1225                1230

Ala Gly Gly Cys Thr Ala Ala Cys Cys Gly Thr Gly Gly Ala Cys
    1235            1240                1245

Ala Ala Gly Ala Gly Cys Ala Gly Gly Thr Gly Gly Cys Ala Gly
    1250            1255                1260

Gly Ala Gly Gly Gly Gly Ala Ala Thr Gly Thr Cys Thr Thr Cys
    1265            1270                1275

Thr Cys Ala Thr Gly Cys Thr Cys Cys Gly Thr Gly Ala Thr Gly
    1280            1285                1290

Cys Ala Thr Gly Ala Gly Gly Cys Thr Cys Thr Gly Cys Ala Cys
    1295            1300                1305

Ala Ala Cys Cys Ala Cys Thr Ala Cys Ala Cys Ala Cys Ala Gly
    1310            1315                1320

Ala Ala Gly Ala Gly Cys Cys Thr Cys Thr Cys Cys Cys Thr Gly
    1325            1330                1335

Thr Cys Thr Cys Thr Gly Gly Gly Thr Gly Gly Cys Gly Gly Ala
    1340            1345                1350

Gly Gly Cys Thr Cys Cys Gly Gly Gly Gly Ala Gly Gly Gly
    1355            1360                1365

Gly Gly Thr Ala Gly Cys Gly Ala Gly Gly Ala Gly Gly Gly
    1370            1375                1380

Gly Gly Ala Thr Cys Cys Cys Ala Gly Gly Thr Thr Cys Ala Gly
    1385            1390                1395

Cys Thr Gly Gly Thr Gly Cys Ala Gly Thr Cys Thr Gly Gly Ala
    1400            1405                1410

Gly Cys Thr Gly Ala Gly Gly Thr Gly Ala Ala Gly Ala Ala Gly
    1415            1420                1425

Cys Cys Thr Gly Gly Gly Gly Cys Cys Thr Cys Ala Gly Thr Gly
    1430            1435                1440

Ala Ala Gly Gly Thr Cys Thr Cys Cys Thr Gly Cys Ala Ala Gly
    1445            1450                1455

Gly Cys Thr Thr Cys Thr Gly Thr Thr Ala Cys Thr Cys Ala
    1460            1465                1470

Thr Thr Cys Ala Cys Thr Gly Ala Cys Thr Ala Cys Ala Ala Cys
    1475            1480                1485

Ala Thr Gly Gly Thr Gly Thr Gly Gly Gly Thr Gly Cys Gly Ala
    1490            1495                1500

Cys Ala Gly Gly Cys Cys Cys Thr Gly Gly Ala Cys Ala Ala
    1505            1510                1515

Thr Gly Cys Cys Thr Thr Gly Ala Gly Thr Gly Gly Ala Thr Gly
    1520            1525                1530

Gly Gly Ala Thr Ala Thr Ala Thr Thr Gly Ala Thr Cys Cys Thr
    1535            1540                1545
```

```
Thr Ala Cys Ala Ala Thr Gly Gly Thr Gly Gly Thr Ala Cys Thr
    1550                1555                1560
Gly Gly Cys Thr Ala Cys Ala Ala Cys Cys Ala Gly Ala Ala Gly
    1565                1570                1575
Thr Thr Cys Gly Ala Gly Gly Cys Ala Gly Ala Gly Thr Cys
    1580                1585                1590
Ala Cys Cys Ala Thr Gly Ala Cys Cys Ala Cys Ala Gly Ala Cys
    1595                1600                1605
Ala Cys Ala Thr Cys Cys Ala Cys Gly Ala Gly Cys Ala Cys Ala
    1610                1615                1620
Gly Cys Cys Thr Ala Cys Ala Thr Gly Gly Ala Gly Cys Thr Gly
    1625                1630                1635
Ala Gly Gly Ala Gly Cys Cys Thr Gly Ala Gly Ala Thr Cys Thr
    1640                1645                1650
Gly Ala Cys Gly Ala Cys Ala Cys Gly Gly Cys Cys Gly Thr Gly
    1655                1660                1665
Thr Ala Thr Thr Ala Cys Thr Gly Thr Gly Cys Gly Ala Gly Ala
    1670                1675                1680
Ala Cys Gly Ala Gly Gly Gly Ala Thr Ala Gly Gly Thr Ala Cys
    1685                1690                1695
Gly Ala Cys Gly Thr Cys Thr Gly Gly Thr Ala Cys Thr Thr Cys
    1700                1705                1710
Gly Ala Thr Gly Thr Cys Thr Gly Gly Gly Gly Cys Cys Ala Gly
    1715                1720                1725
Gly Gly Ala Ala Cys Cys Cys Thr Gly Gly Thr Cys Ala Cys Cys
    1730                1735                1740
Gly Thr Cys Thr Cys Cys Thr Cys Ala Gly Gly Ala Gly Gly Cys
    1745                1750                1755
Gly Gly Ala Gly Gly Thr Thr Cys Cys Gly Gly Gly Gly Gly Ala
    1760                1765                1770
Gly Gly Gly Gly Gly Cys Ala Gly Cys Gly Gly Ala Gly Gly Ala
    1775                1780                1785
Gly Gly Cys Gly Gly Ala Thr Cys Gly Gly Cys Gly Gly Ala
    1790                1795                1800
Gly Gly Ala Gly Gly Ala Ala Gly Thr Gly Gly Ala Gly Gly Cys
    1805                1810                1815
Gly Gly Ala Gly Gly Ala Thr Cys Thr Gly Ala Cys Ala Thr Cys
    1820                1825                1830
Cys Ala Gly Ala Thr Gly Ala Cys Cys Cys Ala Gly Thr Cys Thr
    1835                1840                1845
Cys Cys Ala Thr Cys Thr Thr Cys Cys Gly Thr Gly Thr Cys Thr
    1850                1855                1860
Gly Cys Ala Thr Cys Thr Gly Thr Ala Gly Gly Ala Gly Ala Cys
    1865                1870                1875
Ala Gly Ala Gly Thr Cys Ala Cys Cys Ala Thr Cys Ala Cys Thr
    1880                1885                1890
Thr Gly Thr Ala Ala Gly Gly Cys Cys Ala Gly Thr Cys Ala Gly
    1895                1900                1905
Gly Ala Thr Gly Thr Gly Thr Ala Thr Ala Thr Thr Gly Cys Thr
    1910                1915                1920
Gly Thr Ala Gly Cys Cys Thr Gly Gly Thr Ala Thr Cys Ala Gly
    1925                1930                1935
Cys Ala Gly Ala Ala Ala Cys Cys Ala Gly Gly Gly Ala Ala Ala
```

```
    1940                1945                1950

Gly Cys  Cys Cys Cys Thr Ala  Ala Gly Cys Thr Cys  Cys Thr Gly
    1955                1960                1965

Ala Thr  Cys Thr Ala Thr Thr  Gly Gly Gly Cys Ala  Thr Cys Cys
    1970                1975                1980

Ala Cys  Cys Cys Gly Gly Gly  Ala Cys Ala Cys Thr  Gly Gly Gly
    1985                1990                1995

Gly Thr  Cys Cys Cys Ala Thr  Cys Ala Ala Gly Gly  Thr Thr Cys
    2000                2005                2010

Ala Gly  Cys Gly Gly Cys Ala  Gly Thr Gly Gly Ala  Thr Cys Thr
    2015                2020                2025

Gly Gly  Gly Ala Cys Ala Gly  Ala Thr Thr Thr Cys  Ala Cys Thr
    2030                2035                2040

Cys Thr  Cys Ala Cys Cys Ala  Thr Cys Ala Gly Cys  Ala Gly Cys
    2045                2050                2055

Cys Thr  Gly Cys Ala Gly Cys  Cys Thr Gly Ala Ala  Gly Ala Thr
    2060                2065                2070

Thr Thr  Thr Gly Cys Ala Ala  Cys Thr Thr Ala Cys  Thr Ala Thr
    2075                2080                2085

Thr Gly  Thr Cys Ala Cys Cys  Ala Ala Thr Ala Thr  Ala Gly Cys
    2090                2095                2100

Ala Gly  Cys Thr Ala Thr Cys  Cys Thr Cys Cys Thr  Ala Cys Gly
    2105                2110                2115

Thr Thr  Cys Gly Gly Cys Thr  Gly Cys Gly Gly Gly  Ala Cys Cys
    2120                2125                2130

Ala Ala  Gly Gly Thr Gly Gly  Ala Gly Ala Thr Cys  Ala Ala Ala
    2135                2140                2145

<210> SEQ ID NO 10
<211> LENGTH: 642
<212> TYPE: PRT
<213> ORGANISM: Artificial Sequence
<220> FEATURE:
<223> OTHER INFORMATION: Synthetic Construct

<400> SEQUENCE: 10

Gly Ala Thr Ala Thr Thr Gly Thr Gly Ala Thr Gly Ala Cys Thr Cys
1               5                   10                  15

Ala Gly Thr Cys Thr Cys Cys Ala Gly Cys Cys Ala Cys Cys Cys Thr
            20                  25                  30

Gly Thr Cys Thr Gly Thr Gly Thr Cys Thr Cys Cys Ala Gly Gly Gly
        35                  40                  45

Cys Ala Ala Ala Gly Ala Gly Cys Cys Ala Cys Cys Cys Thr Cys Thr
    50                  55                  60

Cys Cys Thr Gly Cys Ala Gly Gly Gly Cys Cys Ala Gly Thr Cys Ala
65                  70                  75                  80

Ala Ala Ala Thr Ala Thr Thr Ala Gly Gly Ala Ala Thr Ala Ala Cys
                85                  90                  95

Thr Thr Ala Gly Cys Cys Thr Gly Gly Thr Ala Cys Cys Ala Gly Cys
            100                 105                 110

Ala Gly Ala Ala Ala Cys Gly Thr Gly Gly Cys Cys Ala Gly Gly Cys
        115                 120                 125

Thr Cys Cys Cys Ala Gly Gly Cys Thr Cys Cys Thr Cys Ala Thr Cys
    130                 135                 140

Thr Ala Thr Gly Gly Thr Gly Cys Gly Thr Cys Cys Ala Cys Thr Cys
```

-continued

```
145                 150                 155                 160

Gly Gly Gly Cys Cys Ala Cys Ala Gly Gly Thr Ala Thr Cys Cys Cys
                165                 170                 175

Ala Gly Ala Cys Ala Gly Gly Thr Thr Cys Ala Gly Thr Gly Gly Cys
            180                 185                 190

Ala Gly Thr Gly Gly Gly Thr Cys Thr Gly Gly Gly Gly Cys Gly Gly
        195                 200                 205

Ala Cys Thr Thr Cys Ala Cys Thr Cys Thr Cys Ala Cys Cys Ala Thr
    210                 215                 220

Cys Ala Gly Cys Ala Ala Ala Cys Thr Gly Gly Ala Gly Cys Cys Thr
225                 230                 235                 240

Gly Ala Ala Gly Ala Thr Thr Thr Thr Gly Cys Ala Gly Thr Thr Thr
                245                 250                 255

Ala Thr Thr Ala Cys Thr Gly Thr Cys Ala Gly Cys Ala Ala Thr Ala
            260                 265                 270

Thr Gly Gly Thr Ala Gly Cys Thr Cys Ala Cys Cys Thr Cys Gly Gly
        275                 280                 285

Ala Cys Gly Thr Thr Cys Gly Gly Cys Cys Ala Ala Gly Gly Gly Ala
    290                 295                 300

Cys Cys Ala Ala Ala Gly Thr Gly Gly Ala Thr Ala Thr Cys Ala Ala
305                 310                 315                 320

Ala Ala Gly Ala Ala Cys Thr Gly Thr Gly Gly Cys Gly Gly Cys Gly
                325                 330                 335

Cys Cys Ala Thr Cys Thr Gly Thr Cys Thr Thr Cys Ala Thr Cys Thr
            340                 345                 350

Thr Cys Cys Cys Gly Cys Cys Ala Thr Cys Thr Gly Ala Thr Gly Ala
        355                 360                 365

Gly Cys Ala Gly Thr Thr Gly Ala Ala Ala Thr Cys Cys Gly Gly Ala
    370                 375                 380

Ala Cys Thr Gly Cys Cys Thr Cys Thr Gly Thr Thr Gly Thr Gly Thr
385                 390                 395                 400

Gly Cys Cys Thr Gly Cys Thr Gly Ala Ala Thr Ala Ala Cys Thr Thr
                405                 410                 415

Cys Thr Ala Thr Cys Cys Cys Ala Gly Ala Gly Ala Gly Gly Cys Cys
            420                 425                 430

Ala Ala Ala Gly Thr Ala Cys Ala Gly Thr Gly Gly Ala Ala Gly Gly
        435                 440                 445

Thr Gly Gly Ala Thr Ala Ala Cys Gly Cys Cys Cys Thr Cys Cys Ala
    450                 455                 460

Ala Thr Cys Gly Gly Gly Thr Ala Ala Cys Thr Cys Cys Cys Ala Gly
465                 470                 475                 480

Gly Ala Gly Ala Gly Thr Gly Thr Cys Ala Cys Ala Gly Ala Gly Cys
                485                 490                 495

Ala Gly Gly Ala Cys Ala Gly Cys Ala Ala Gly Gly Ala Cys Ala Gly
            500                 505                 510

Cys Ala Cys Cys Thr Ala Cys Ala Gly Cys Cys Thr Cys Ala Gly Cys
        515                 520                 525

Ala Gly Cys Ala Cys Cys Cys Thr Gly Ala Cys Gly Cys Thr Gly Ala
    530                 535                 540

Gly Cys Ala Ala Ala Gly Cys Ala Gly Ala Cys Thr Ala Cys Gly Ala
545                 550                 555                 560

Gly Ala Ala Ala Cys Ala Cys Ala Ala Ala Gly Thr Cys Thr Ala Cys
                565                 570                 575
```

```
Gly Cys Cys Thr Gly Cys Gly Ala Ala Gly Thr Cys Ala Cys Cys
            580                 585                 590
Ala Thr Cys Ala Gly Gly Cys Cys Thr Gly Ala Gly Cys Thr Cys
            595                 600                 605
Gly Cys Cys Cys Gly Thr Cys Ala Cys Ala Ala Gly Ala Gly Cys
            610                 615                 620
Thr Thr Cys Ala Ala Cys Ala Gly Gly Gly Ala Gly Ala Gly Thr
625                 630                 635                 640
Gly Cys
```

```
<210> SEQ ID NO 11
<211> LENGTH: 165
<212> TYPE: PRT
<213> ORGANISM: Artificial Sequence
<220> FEATURE:
<223> OTHER INFORMATION: Synthetic Construct

<400> SEQUENCE: 11

Ala Pro Met Ala Glu Gly Gly Gln Asn His His Glu Val Val Lys
1               5                   10                  15
Phe Met Asp Val Tyr Gln Arg Ser Tyr Cys His Pro Ile Glu Thr Leu
                20                  25                  30
Val Asp Ile Phe Gln Glu Tyr Pro Asp Glu Ile Glu Tyr Ile Phe Lys
            35                  40                  45
Pro Ser Cys Val Pro Leu Met Arg Cys Gly Gly Cys Cys Asn Asp Glu
        50                  55                  60
Gly Leu Glu Cys Val Pro Thr Glu Glu Ser Asn Ile Thr Met Gln Ile
65                  70                  75                  80
Met Arg Ile Lys Pro His Gln Gly Gln His Ile Gly Glu Met Ser Phe
                85                  90                  95
Leu Gln His Asn Lys Cys Glu Cys Arg Pro Lys Lys Asp Arg Ala Arg
            100                 105                 110
Gln Glu Asn Pro Cys Gly Pro Cys Ser Glu Arg Arg Lys His Leu Phe
        115                 120                 125
Val Gln Asp Pro Gln Thr Cys Lys Cys Ser Cys Lys Asn Thr Asp Ser
    130                 135                 140
Arg Cys Lys Ala Arg Gln Leu Glu Leu Asn Glu Arg Thr Cys Arg Cys
145                 150                 155                 160
Asp Lys Pro Arg Arg
                165
```

```
<210> SEQ ID NO 12
<211> LENGTH: 478
<212> TYPE: PRT
<213> ORGANISM: Artificial Sequence
<220> FEATURE:
<223> OTHER INFORMATION: Synthetic Construct

<400> SEQUENCE: 12

Tyr Asn Asn Phe Arg Lys Ser Met Asp Ser Ile Gly Lys Lys Gln Tyr
1               5                   10                  15
Gln Val Gln His Gly Ser Cys Ser Tyr Thr Phe Leu Leu Pro Glu Met
                20                  25                  30
Asp Asn Cys Arg Ser Ser Ser Ser Pro Tyr Val Ser Asn Ala Val Gln
            35                  40                  45
Arg Asp Ala Pro Leu Glu Tyr Asp Ser Val Gln Arg Leu Gln Val
        50                  55                  60
```

```
Leu Glu Asn Ile Met Glu Asn Thr Gln Trp Leu Met Lys Leu Glu
 65                  70                  75                  80

Asn Tyr Ile Gln Asp Asn Met Lys Lys Glu Met Val Glu Ile Gln Gln
                 85                  90                  95

Asn Ala Val Gln Asn Gln Thr Ala Val Met Ile Glu Ile Gly Thr Asn
            100                 105                 110

Leu Leu Asn Gln Thr Ala Glu Gln Thr Arg Lys Leu Thr Asp Val Glu
            115                 120                 125

Ala Gln Val Leu Asn Gln Thr Thr Arg Leu Glu Leu Gln Leu Leu Glu
130             135                 140

His Ser Leu Ser Thr Asn Lys Leu Glu Lys Gln Ile Leu Asp Gln Thr
145                 150                 155                 160

Ser Glu Ile Asn Lys Leu Gln Asp Lys Asn Ser Phe Leu Glu Lys Lys
                165                 170                 175

Val Leu Ala Met Glu Asp Lys His Ile Ile Gln Leu Gln Ser Ile Lys
            180                 185                 190

Glu Glu Lys Asp Gln Leu Gln Val Leu Val Ser Lys Gln Asn Ser Ile
            195                 200                 205

Ile Glu Glu Leu Glu Lys Lys Ile Val Thr Ala Thr Val Asn Asn Ser
210                 215                 220

Val Leu Gln Lys Gln Gln His Asp Leu Met Glu Thr Val Asn Asn Leu
225                 230                 235                 240

Leu Thr Met Met Ser Thr Ser Asn Ser Ala Lys Asp Pro Thr Val Ala
                245                 250                 255

Lys Glu Glu Gln Ile Ser Phe Arg Asp Cys Ala Glu Val Phe Lys Ser
            260                 265                 270

Gly His Thr Thr Asn Gly Ile Tyr Thr Leu Thr Phe Pro Asn Ser Thr
            275                 280                 285

Glu Glu Ile Lys Ala Tyr Cys Asp Met Glu Ala Gly Gly Gly Gly Trp
290                 295                 300

Thr Ile Ile Gln Arg Arg Glu Asp Gly Ser Val Asp Phe Gln Arg Thr
305                 310                 315                 320

Trp Lys Glu Tyr Lys Val Gly Phe Gly Asn Pro Ser Gly Glu Tyr Trp
                325                 330                 335

Leu Gly Asn Glu Phe Val Ser Gln Leu Thr Asn Gln Gln Arg Tyr Val
            340                 345                 350

Leu Lys Ile His Leu Lys Asp Trp Glu Gly Asn Glu Ala Tyr Ser Leu
            355                 360                 365

Tyr Glu His Phe Tyr Leu Ser Ser Glu Glu Leu Asn Tyr Arg Ile His
            370                 375                 380

Leu Lys Gly Leu Thr Gly Thr Ala Gly Lys Ile Ser Ser Ile Ser Gln
385                 390                 395                 400

Pro Gly Asn Asp Phe Ser Thr Lys Asp Gly Asp Asn Asp Lys Cys Ile
                405                 410                 415

Cys Lys Cys Ser Gln Met Leu Thr Gly Gly Trp Trp Phe Asp Ala Cys
            420                 425                 430

Gly Pro Ser Asn Leu Asn Gly Met Tyr Tyr Pro Gln Arg Gln Asn Thr
            435                 440                 445

Asn Lys Phe Asn Gly Ile Lys Trp Tyr Tyr Trp Lys Gly Ser Gly Tyr
            450                 455                 460

Ser Leu Lys Ala Thr Thr Met Met Ile Arg Pro Ala Asp Phe
465                 470                 475
```

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Gly Gly Gly Gly Ser Gly Gly Gly Gly Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 20
<212> TYPE: PRT
<213> ORGANISM: Artificial Sequence
<220> FEATURE:
<223> OTHER INFORMATION: Synthetic Construct

<400> SEQUENCE: 15

Gly Gly Gly Gly Ser Gly Gly Gly Gly Ser Gly Gly Gly Gly Ser Gly
1               5                   10                  15

Gly Gly Gly Ser
            20

<210> SEQ ID NO 16
<211> LENGTH: 25
<212> TYPE: PRT
<213> ORGANISM: Artificial Sequence
<220> FEATURE:
<223> OTHER INFORMATION: Synthetic Construct

<400> SEQUENCE: 16

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Gly Gly Gly Ser Gly Gly Gly Gly Ser Gly Gly Gly Gly Ser
1               5                   10

VEGFA/ANG2 COMPOUNDS

The present invention relates to the field of medicine. More particularly, the present invention relates to compounds that bind to human vascular endothelial growth factor A (VEGFA) and human angiopoietin-2 (Ang2), and may be useful for treating angiogenic eye diseases, such as diabetic and other proliferative retinopathies, and for cancer, especially solid tumors driven by VEGFA and Ang2, including gastric, lung, hepatocellular carcinoma, ovarian, colorectal, and breast cancers.

A hallmark of cancer is persistent new blood vessel formation, called angiogenesis. The vascular endothelial growth factor (VEGF) pathway is an important signaling cascade in the regulation of angiogenesis; human VEGFA is a key ligand in the VEGF pathway.

Angiopoietin-1 (Ang1) and Ang2 are members of another key pathway that regulate angiogenesis; Ang1 and Ang2 are secreted factors that bind to the endothelial cell-specific receptor tyrosine kinase Tie2. Ang1 is constitutively secreted by pericytes and stabilizes blood vessel integrity via the Tie2 receptor. Ang2 is released from endothelial cells only in response to stimulus (e.g. wound healing, tumor growth) and facilitates blood vessel sprouting and inhibits pericyte-endothelial cell interaction via Tie2 signaling. An antibody against human Ang2, when dosed in combination with the VEGF blocker aflibercept, has been shown to inhibit tumor growth and to decrease tumor vascularity in mouse xenograft tumor models (Daly et al., Cancer Res (2013) 73(1):108). Multiple investigational Ang2 antibodies are currently in clinical trials.

Inhibition of both the VEGF and Ang/Tie2 pathways of angiogenesis has been proposed for the potential to improve the outcome against cancer (see, for example, Daly et al., Cancer Res (2013) 73:108). Currently, co-administration of a VEGFA antibody and Ang-2 antibody would require either injections or infusions of two separate products or administration of a co-formulation of an antibody mixture. Separate administration would permit flexibility of dose amount and timing, but would be a potential issue for patient compliance and convenience due to increased infusion time. A co-formulation might also provide some flexibility of dosage amounts, but can be challenging to find formulation conditions that permit chemical and physical stability of both antibodies due to different molecular characteristics of the two different antibodies. Furthermore, co-administration or co-formulation involves the additive costs of two drug therapies.

WO2012/009705 disclosed complexes containing one or more modular recognition domains (MRDs) attached to scaffolds that include antibodies. Ang2 was listed as contemplated for the MRD portion of the complex, and a VEGFA antibody was specified as an antibody which MRDs could be attached. A MRD against Ang2 attached to a VEGFA antibody was not exemplified. WO2010/040508, WO2011/117329, and WO2012/131078 claim bispecific antibodies to VEGFA and Ang-2.

There remains a need to provide compounds that inhibit two angiogenesis pathways by binding and neutralizing both human VEGFA and human Ang2. In particular, there remains a need to provide compounds that inhibit two angiogenesis pathways by binding and neutralizing both human VEGFA and human Ang2, and without compromising significant Ang2 in vitro binding activity due to the use of an Ang2 scFv, and without compromising significant in vitro cell-based assay activity due to the combination of the VEGFA antibody and Ang2 scFv into one compound. There remains a need to provide compounds that neutralize Ang2 mediated phosphorylation of Tie2, but not Ang1 mediated phosphorylation.

Accordingly, an embodiment of the present invention provides a compound, comprising an antibody fused by two linkers to two single chain fragment variable (scFv) polypeptides, wherein:
 a) the antibody comprises two identical heavy chains (HCs) and two identical light chains (LCs), wherein each HC comprises a heavy chain variable region (HCVR) whose amino acid sequence is given in SEQ ID NO: 1, and wherein each LC comprises a light chain variable region (LCVR) whose amino acid sequence is given in SEQ ID NO: 4,
 b) the two scFv polypeptides are identical and each comprise an HCVR operably linked to an LCVR, wherein each HCVR has the amino acid sequence given in SEQ ID NO: 7, and wherein each LCVR has the amino acid sequence given in SEQ ID NO: 8, and
 c) the two linkers are identical glycine-rich linkers that each operably link the carboxy-terminus of one HC of the antibody to the amino-terminus of one of the scFv polypeptides.

In a further embodiment, the present invention provides a compound comprising an antibody fused by two linkers to two scFv polypeptides, wherein the two scFv polypeptides each comprise the carboxy-terminus of the HCVR of one scFv polypeptide operably linked to the amino-terminus of the LCVR of one scFv polypeptide.

In an embodiment, the present invention provides a compound comprising an antibody fused by two linkers to two scFv polypeptides, wherein the antibody comprises two heavy chains (HCs) and two light chains (LCs), wherein each HC has the amino acid sequence given in SEQ ID NO: 2, and each LC has the amino acid sequence given in SEQ ID NO: 5.

In an embodiment, the present invention provides a compound comprising an antibody fused by two linkers to two scFv polypeptides, wherein each scFv polypeptide has the identical amino acid sequence, which is that given in SEQ ID NO: 6.

In an embodiment, the present invention provides a compound comprising two first polypeptides and two second polypeptides wherein each of the first polypeptides has the amino acid sequence of SEQ ID NO: 3, and each of the second polypeptides has the amino acid sequence of SEQ ID NO: 5. As shown in Table 1, the two first polypeptides comprise the HC of the antibody, the linker, and the scFv polypeptide; the two second polypeptides comprise the LC of the antibody.

In an embodiment, the present invention further provides a compound comprising two first polypeptides and two second polypeptides wherein each of the first polypeptides forms an inter-chain disulfide bond with each of the second polypeptides, and the first polypeptide forms two inter-chain disulfide bonds with the other first polypeptide, and each of the first polypeptides forms seven intra-chain disulfide bonds.

In an embodiment, the present invention provides a compound that binds human VEGFA and human Ang2 comprising an antibody that binds human VEGFA (SEQ ID NO: 11) fused by two linkers to two scFv polypeptides that bind human Ang2 (SEQ ID NO: 12), wherein:
 a) the antibody comprises two identical heavy chains (HCs) and two identical light chains (LCs), wherein each HC comprises a heavy chain variable region (HCVR) whose amino acid sequence is given in SEQ ID NO: 1, and wherein each LC comprises a light chain variable region (LVCR) whose amino acid sequence is given in SEQ ID NO: 4, b) the two scFv polypeptides are identical and each comprise an HCVR operably linked to an LCVR, wherein each HCVR has the amino acid sequence given in SEQ ID NO: 7, and wherein each LCVR has the amino acid sequence given in SEQ ID NO: 8, and c) the two linkers are identical glycine-rich linkers that each operably link the carboxy-terminus of one HC of the antibody to the amino-terminus of one of the scFv polypeptides.

In a further embodiment, the present invention provides a compound that binds human VEGFA and human Ang2 comprising an antibody that binds human VEGFA (SEQ ID NO: 11) fused by two linkers to two scFv polypeptides that bind human Ang2 (SEQ ID NO: 12), wherein the carboxy-terminus of the HCVR of each scFv polypeptide is operably linked to the amino-terminus of the LCVR.

In an embodiment, the present invention provides a compound that binds human VEGFA and human Ang2 comprising an antibody that binds human VEGFA (SEQ ID NO: 11) fused by two linkers to two scFv polypeptides that bind human Ang2 (SEQ ID NO: 12), wherein the antibody comprises two heavy chains (HCs) and two light chains (LCs), wherein each HC has the amino acid sequence given in SEQ ID NO: 2, and each LC has the amino acid sequence given in SEQ ID NO: 5.

In an embodiment, the present invention provides a compound that binds human VEGFA and human Ang2 comprising an antibody that binds human VEGFA (SEQ ID NO: 11) fused by two linkers to two scFv polypeptides that bind human Ang2 (SEQ ID NO: 12), wherein each scFv polypeptide has the identical amino acid sequence, which is that given in SEQ ID NO: 6.

In an embodiment, the present invention provides a compound that binds human VEGFA (SEQ ID NO: 11) and human Ang2 (SEQ ID NO: 12) comprising two first polypeptides and two second polypeptides wherein each of the first polypeptides has the amino acid sequence of SEQ ID NO: 3, and each of the second polypeptides has the amino acid sequence of SEQ ID NO: 5.

In an embodiment, the present invention further provides a compound that binds human VEGFA (SEQ ID NO: 11) and human Ang2 (SEQ ID NO: 12) comprising two first polypeptides and two second polypeptides wherein each of the first polypeptides forms an inter-chain disulfide bond with each of the second polypeptides, and the first polypeptide forms two inter-chain disulfide bonds with the other first polypeptide, and each of the first polypeptides forms seven intra-chain disulfide bonds.

In an embodiment, the present invention provides an antibody that binds human VEGFA (SEQ ID NO: 11), comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 4, and the HCVR has the amino acid sequence given in SEQ ID NO: 1.

In an embodiment, the present invention provides an antibody that binds human VEGFA (SEQ ID NO: 11), comprising a light chain (LC) and a heavy chain (HC), wherein the LC has the amino acid sequence given in SEQ ID NO: 5, and the HC has the amino acid sequence given in SEQ ID NO: 2.

In a further embodiment, the present invention provides an antibody that binds VEGFA (SEQ ID NO: 11), comprising two light chains and two heavy chains, wherein each light chain has the amino acid sequence given in SEQ ID NO: 5, and each heavy chain has the amino acid sequence given in SEQ ID NO: 2.

In an embodiment, the present invention provides a mammalian cell comprising a DNA molecule comprising a polynucleotide sequence encoding a first polypeptide given by SEQ ID NO: 3 and a polynucleotide sequence encoding a second polypeptide given by SEQ ID NO: 5, wherein the cell is capable of expressing a compound comprising the first polypeptide and the second polypeptide.

In an embodiment, the present invention provides a process for producing a compound comprising two first polypeptides given by SEQ ID NO: 3, and two second polypeptides given by SEQ ID NO: 5, comprising cultivating the mammalian cell of the present invention under conditions such that the compound is expressed, and recovering the expressed compound.

In an embodiment of the above-described processes, the two polynucleotide sequences in the mammalian cell of the present invention are part of the same nucleic acid molecule (SEQ ID NO: 9 and SEQ ID NO:10).

In an embodiment, the present invention provides a compound obtainable by one of the aforementioned processes.

In an embodiment, the present invention provides a pharmaceutical composition, comprising a compound of the present invention, and an acceptable carrier, diluent, or excipient.

In an embodiment, the present invention provides a method of treating cancer, comprising administering to a patient in need thereof, an effective amount of a compound of the present invention. In a further embodiment, the present invention provides a method of treating cancer, comprising administering to a patient in need thereof, an effective amount of a compound of the present invention, wherein the cancer is breast cancer, lung cancer, ovarian cancer, gastric cancer, colorectal cancer, hepatocellular carcinoma, or Von Hippel-Lindau syndrome.

In a further embodiment, these methods comprise the administration of an effective amount of the compound of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab.

In a further embodiment, these methods comprise the administration of an effective amount of the compound of the present invention in simultaneous, separate, or sequential combination with one or more immuno-oncology agents selected from the group consisting of nivolumab, ipilimumab, pidilizumab, pembrolizumab, and durvalumab.

In an embodiment, the present invention provides a method of treating proliferative retinopathy, comprising administering to a patient in need thereof, an effective amount of a compound of the present invention. In a further embodiment, the present invention provides a method of treating proliferative retinopathy, comprising administering to a patient in need thereof, an effective amount of a compound of the present invention, wherein the proliferative retinopathy is diabetic retinopathy, or retinopathy of prematurity.

In an embodiment, the present invention provides a method of treating angiogenic eye disease, comprising administering to a patient in need thereof, an effective amount of a compound of the present invention. In a further embodiment, the present invention provides a method of treating angiogenic eye disease, comprising administering to a patient in need thereof, an effective amount of a compound of the present invention, wherein the angiogenic eye disease is neovascular glaucoma, age-related macular degeneration, diabetic macular edema, conical neovascularization, conical graft neovascularization, conical graft rejection, retinal/choroidal neovascularization, neovascularization of the angle (rubeosis), ocular neovascular disease, vascular restenosis, or arteriovenous malformations (AVM).

In an embodiment, the present invention provides a compound of the present invention, for use in therapy. In an embodiment, the present invention provides a compound of the present invention, for use in the treatment of cancer. In a further embodiment, the present invention provides a compound of the present invention, for use in the treatment of cancer, wherein the cancer is breast cancer, lung cancer, ovarian cancer, gastric cancer, colorectal cancer, or hepatocellular carcinoma. In a further embodiment, for use in the treatment of cancer, the compound of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab.

In a further embodiment, for use in the treatment of cancer, the compound of the present invention in simultaneous, separate, or sequential combination with one or more immuno-oncology agents selected from the group consisting of nivolumab, ipilimumab, pidilizumab, pembrolizumab, and durvalumab.

In an embodiment, the present invention provides a compound of the present invention, for use in the treatment of proliferative retinopathy. In a further embodiment, the present invention provides a compound of the present invention, for use in the treatment of proliferative retinopathy, wherein the proliferative retinopathy is diabetic retinopathy, retinopathy of prematurity, sickle cell retinopathy, post traumatic retinopathy, a hyperviscosity syndrome, an aortic arch syndrome, an ocular ischemic syndrome, carotid-cavernous fistula, multiple sclerosis, retinal vasculitis, systemic lupus erythematosus, arteriolitis with SS-A autoantibody, acute multifocal hemorrhagic vasculitis, vasculitis resulting from infection, vasculitis resulting from Behçet's disease, sarcoidosis, coagulopathies, a sickling hemoglobinopathy, AC and C-β thalassemia, small vessel hyalinosis, incontinentia pigmenti, Eales' disease, branch retinal artery or vein occlusion, frosted branch angiitis, idiopathic retinal vasculitis, an aneurysm, neuroretinitis, retinal embolization, retinopathy of prematurity, uveitis, pars planitis, acute retinal necrosis, birdshot retinochoroidopathy, long-standing retinal detachment, choroidal melanoma, radiation retinopathy, familial exudative vitreoretinopathy, inherited retinal venous beading, retinoschisis, retinitis pigmentosa, or autosomal dominant vitreoretinochoroidopathy.

In an embodiment, the present invention provides a compound of the present invention, for use in the treatment of angiogenic eye disease. In a further embodiment, the present invention provides a compound of the present invention, for use in the treatment of angiogenic eye disease, wherein the angiogenic eye disease is neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, or arteriovenous malformations (AVM). Examples of age-related macular degeneration are non-neovascular (also known as "dry") and neovascular (also known as "wet" or "exudative") macular degeneration.

In an embodiment, the present invention provides the use of a compound of the present invention for the manufacture of a medicament for the treatment of cancer. In a further embodiment, the present invention provides the use of a compound of the present invention for the manufacture of a medicament for the treatment of cancer, wherein the cancer is breast cancer, lung cancer, ovarian cancer, gastric cancer, colorectal cancer, hepatocellular carcinoma, or Von Hippel-Lindau syndrome.

In a further embodiment, the present invention provides the use of a compound of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab for the manufacture of a medicament for the treatment of cancer.

In a further embodiment, the present invention provides the use of a compound of the present invention in simultaneous, separate, or sequential combination with one or more immuno-oncology agents selected from the group consisting of nivolumab, ipilimumab, pidilizumab, pembrolizumab, and durvalumab for the manufacture of a medicament for the treatment of cancer.

In an embodiment, the present invention provides the use of a compound of the present invention for the manufacture of a medicament for the treatment of proliferative retinopathy. In a further embodiment, the present invention provides the use of a compound of the present invention for the manufacture of a medicament for the treatment of proliferative retinopathy, wherein the proliferative retinopathy is diabetic retinopathy, retinopathy of prematurity, sickle cell retinopathy, post traumatic retinopathy, a hyperviscosity syndrome, an aortic arch syndrome, an ocular ischemic syndrome, carotid-cavernous fistula, multiple sclerosis, retinal vasculitis, systemic lupus erythematosus, arteriolitis with SS-A autoantibody, acute multifocal hemorrhagic vasculitis, vasculitis resulting from infection, vasculitis resulting from Behçet's disease, sarcoidosis, coagulopathies, a sickling hemoglobinopathy, AC and C-β thalassemia, small vessel hyalinosis, incontinentia pigmenti, Eales' disease, branch retinal artery or vein occlusion, frosted branch angiitis, idiopathic retinal vasculitis, an aneurysm, neuroretinitis, retinal embolization, retinopathy of prematurity, uveitis, pars planitis, acute retinal necrosis, birdshot retinochoroidopathy, long-standing retinal detachment, choroidal melanoma, radiation retinopathy, familial exudative vitreoretinopathy, inherited retinal venous beading, retinoschisis, retinitis pigmentosa, or autosomal dominant vitreoretinochoroidopathy.

In an embodiment, the present invention provides the use of a compound of the present invention for the manufacture of a medicament for the treatment of angiogenic eye disease. In a further embodiment, the present invention provides the use of a compound of the present invention for the manufacture of a medicament for the treatment of angiogenic eye disease, wherein the angiogenic eye disease is neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, or arteriovenous malformations (AVM). Examples of age-related macular degeneration are non-neovascular (also known as "dry") and neovascular (also known as "wet" or "exudative") macular degeneration.

A compound of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in a compound of the present invention.

The antibody portion of the compound of the present invention is designed to have engineered CDRs and have some portions of the antibody (all or parts of the frameworks, hinge regions, and constant regions) to be of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and those with engineered mutations. The antibody portion of the compound of the present invention may comprise framework, hinge, or constant regions derived from a fully human framework, hinge, or constant region containing one or more amino acid substitutions, deletions, or additions therein. Further, the antibody portion of the compound of the present invention is preferably substantially non-immunogenic in humans.

The antibody portion of the compound of the present invention is an IgG type antibody and has four amino acid chains (two "heavy" chains and two "light" chains) that are covalently stabilized via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, the antibody portion of the compound of the present invention contains an Fc portion which is derived from human IgG$_4$ Fc region because of a reduced ability to engage Fc receptor-mediated inflammatory mechanisms or to activate complement resulting in reduced effector function.

Further, the antibody portion of certain compounds of the present invention contains an IgG$_4$-PAA Fc portion. The IgG$_4$-PAA Fc portion has a serine to proline mutation at position 231, a phenylalanine to alanine mutation at position 237, and a leucine to alanine mutation at position 238. The S231P mutation is a hinge mutation that prevents half-antibody formation (phenomenon of dynamic exchange of half-molecules in IgG$_4$ antibodies). The F237A and L238A mutations further reduce effector function of the already low human IgG$_4$ isotype.

An isolated DNA molecule encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

A "single chain fragment variable" or "scFv" or "scFv polypeptide" refers to an engineered, non-naturally occurring single folded polypeptide comprising the LCVR and the HCVR of an antibody linked through a scFv linker molecule. The scFv polypeptide portion of the compound of the present invention is an engineered, non-naturally occurring scFv that has been designed to have engineered CDRs and have some portions of the scFv (all or parts of the frameworks) to be of human origin that are identical with or substantially identical (substantially human) with frameworks derived from human genomic sequences. Fully human frameworks are those human germline sequences as well as sequences with naturally-occurring somatic mutations and those with engineered mutations. The scFv polypeptide portion of the compound of the present invention may comprise framework derived from a fully human framework containing one or more amino acid substitutions, deletions, or additions therein. Further, the scFv polypeptide portion of the compound of the present invention is preferably substantially non-immunogenic in humans. Optionally, the scFv polypeptide portion of the compound can have disulfides from cysteine 44 in HCVR and cysteine 100 in LCVR (Cys44 and Cys100 numbering corresponds with amino acid numbering of HCVR and LCVR of the scFv polypeptide; for the numbering in the HC of antibody+linker+scFv polypeptide, it is Cys507 and Cys709). In such a scFv polypeptide, the HCVR and LCVR domains can be either in the HCVR–scFv linker–LCVR or LCVR–scFv linker–HCVR order. The scFv linker can be a flexible glycine-rich peptide linker which enables the HCVR and LCVR chains to be folded as a functional monomeric unit for recognizing an antigen. Optionally, the scFv linker is a glycine-rich linker such as a 2× G4S linker, a 3× G4S linker, a 4× G4S linker, or a 5× G4S linker.

The term "linker" and "scFv linker" both refer to glycine-rich peptide linkers. The "linkers" are utilized in certain embodiments of the invention to link the antibody to the scFv, and the "scFv linkers" are utilized in certain embodiments of the invention to link the LCVR of the scFv to the HCVR of the scFv. Preferably, the peptide linkers are glycine-rich peptides with at least 5 amino acids, preferably of at least 10 amino acids, more preferably between 10 and 50 amino acids. In some embodiments of the present invention, said glycine-rich peptide linker is $(G_xS)_n$ with G=glycine, S=serine, (x=3 and n=3, 4, 5 or 6) or (x=4 and n=2, 3, 4 or 5). For example, in some embodiments of the present invention, said glycine-rich peptide linker is $(G_xS)_n$ with G=glycine, S=serine, x=4 and n=2, 3, 4 or 5 (i.e., GGGGSGGGGS (SEQ ID NO: 13), GGGGSGGGGSGGGGS (SEQ ID NO: 14), GGGGSGGGGSGGGGSGGGGS (SEQ ID NO: 15), or GGGGSGGGGSGGGGSGGGGSGGGGS (SEQ ID NO: 16), respectively. In some embodiments of the present invention where the last amino acid in the antibody constant region is a glycine, said glycine-rich peptide linker is GGGSGGGGSGGGGS (SEQ ID NO:17).

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The compound of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the compound and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice*, 3rd Edition, Springer, N.Y. (1994).

In another embodiment of the present invention, the compound, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The compound of the present invention, or pharmaceutical compositions comprising the same, may be administered parenterally (e.g., intravitreal, intraocular, subconjunctival, subcutaneously or via intravenous injection or implant). A compound of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy*, 19$^{th}$ ed. (1995), A. Gennaro et al., Mack Publishing Co.) and comprise a compound, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease. A patient refers to a mammal, preferably a human with a disease, disorder, or condition that would benefit from inhibition of VEGFA and/or Ang2.

"Binds" as used herein in reference to the affinity of a compound, antibody, or scFv polypeptide for human VEGFA or human Ang2 is intended to mean, unless indicated otherwise, a $K_D$ of less than about $1\times10^{-8}$ M, preferably, less than about $1\times10^{-9}$ M as determined by common methods known in the art, including by use of a surface plasmon resonance (SPR) biosensor at 25° C. or 37° C. essentially as described herein. The term "selective" or "selectivity" used herein in reference to a compound of the present invention refers to a compound that binds a target, such as human Ang2, with a $K_D$ about 1000-, 500-, 200-, 100-, 50-, or about 10-fold lower than the compound binds other proteins, including member of the target family such as human Ang1, as measured by surface plasmon resonance at 25° C. or 37° C. Additionally, or alternatively, an Ang2 selective compound of the present invention binds human Ang2 but does not bind or only minimally binds human Ang1 when assayed by the methods described in the Example herein below.

"Effective amount" means the amount of a compound of the present invention or pharmaceutical composition comprising a compound of the present invention that will elicit the biological or medical response of or desired therapeutic effect on a tissue, system, animal, mammal or human that is being sought by the researcher, medical doctor, or other clinician. An effective amount of the compound may vary according to factors such as the disease state, age, sex, and weight of the individual, and the ability of the compound to elicit a desired response in the individual. An effective amount is also one in which any toxic or detrimental effect of the compound is outweighed by the therapeutically beneficial effects.

This invention is further illustrated by the following non-limiting examples.

EXAMPLE 1: COMPOUND EXPRESSION AND PURIFICATION

For Example 1 (Compound A) as shown in Table 1, the two first polypeptides (HC of antibody-linker-scFv of Compound A) have the amino acid sequence of SEQ ID NO: 3, and the two second polypeptides (LC of antibody of Compound A) have the amino acid sequence of SEQ ID NO: 5.

The polypeptide of the antibody portion, the scFv portion, and the antibody-linker-scFv of Compound A, and the nucleotide sequences encoding the same, are listed below in the section entitled "Amino Acid and Nucleotide Sequences."

The compounds of the present invention, including, but not limited to Compound A, can be made and purified essentially as follows. An appropriate host cell, such as HEK 293 or CHO, can be either transiently or stably transfected with an expression system for secreting compounds using an optimal predetermined HC-linker-scFv:LC vector ratio (such as 1:3 or 1:2) or a single vector system encoding both HC-linker-scFv and LC. Clarified media, into which the compound has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound compound may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Compound fractions may be detected, such as by SDS-PAGE, and then may be pooled. Further purification is optional, depending on the intended use. The compound may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the compound after these chromatography steps is greater than 95%. The product may be immediately frozen at −70° C. or may be lyophilized

TABLE 1

|  | Compound A |
|---|---|
| HCVR of antibody | 1 |
| HC of antibody | 2 |
| HC of antibody + linker + scFv polypeptide | 3 |
| LCVR of antibody | 4 |
| LC of antibody | 5 |
| scFv polypeptide | 6 |
| HCVR of scFv polypeptide | 7 |
| LCVR of scFv polypeptide | 8 |

Assays
Binding Kinetics, Affinity, and Selectivity

The binding kinetics, affinity, and selectivity to human Ang2 and to human VEGFA, for compounds of the present invention, are determined by use of a surface plasmon resonance (SPR) biosensor such as a Biacore® 2000, Biacore® 3000, or a Biacore® T100 (GE HealthCare), or alternatively by kinetic exclusion assay methods associated with Kinexa 3000 or 3200 (Sapidyne Instruments) according to methods known in the art.

Affinity Measurement Using Biacore SPR

The kinetics and equilibrium dissociation constant ($K_D$) for soluble full length human Ang2 and human VEGFA is determined for compounds of the present invention at 25° C. using or Biacore surface plasmon resonance assay methods. Human Ang2 is from R&D Systems (#623-AN-01M/CF) and human VEGFA165 is from R&D systems (#293-VE-001MG/CF), Peprotech (#00-20), or prepared by recombinant expression methods. Protein A surface for capture of antibodies is prepared using the following methods. Immobilization of soluble Protein A (Calbiochem #539202) on a CM4 (GE Healthcare #BR-1005-34) or CM5 (GE Healthcare #BR-1000-99) is prepared using EDC/NHS amine coupling method (GE Healthcare #BR-1000-50). Briefly, the surfaces of all four flow cells is activated by injecting a 1:1 mixture of EDC/NHS for seven minutes at 10 μL/min After which, soluble protein A is diluted to 50-100 μg/mL in 10 mM acetate buffer, pH 4.5, and immobilized for seven minutes onto flow cell (Fc) 2, 3 or 4 at a flow rate of 10 μL/min. Unreacted sites still remaining on the chip surface are blocked with a seven minute injection of ethanolamine at 10 μL/min Running buffer is HBS-EP+ (GE Healthcare #BR-1006-69) with addition of 100 mM NaCl. Compound samples are prepared at 1 μg/mL by dilution into running buffer. Human Ang2 or human VEGFA165 ranging from 50 nM to 1.56 nM is prepared in running buffer using a two-fold serial dilution. Each analysis cycle consists of a series of five separate steps: (1) capture of compound onto separate flow cells (Fc2, Fc3, and Fc4), (2) injection (using kinject) of 250 μL (300-second surface contact time) of discrete concentrations of human Ang2 or human VEGFA165 over all Fc at 50 μL/min, (3) return to buffer flow for 20 minutes to monitor dissociation phase, (4) regeneration of chip surfaces with a 10 μL (30-second contact time) injection of 10 mM glycine, pH1.5, (5) equilibration of chip surface with a 15 μL (45-second contact time) injection of HBS-EP+ running buffer. Resultant data is processed using standard double-referencing and fit to a 1:1 binding model using Biacore 2000 Evaluation software, version 4.1, to determine the association rate ($k_{on}$, $M^{-1}s^{-1}$ units), dissociation rate ($k_{off}$, $s^{-1}$ units). Calculation of the equilibrium dissociation constant ($K_D$) is calculated from the following relationship, $K_D = k_{off}/k_{on}$, and is presented in molar units.

In experiments performed essentially as described in this assay, the parental anti-VEGFA antibody of Compound A exhibits a $K_D$ of 13.2 pM for human VEGFA165. Compound A, a Mab-scFv fusion which combines a parental anti-VEGFA antibody with a C-terminal heavy chain scFv composed of HCVR and LCVR from an Ang2 Mab, exhibits a $K_D$ of 83.2 pM (Table 2). The binding affinity ($K_D$) of Compound A for human Ang2 evaluated using Biacore SPR at 25° C. is 136 pM (Table 3).

TABLE 2

| Biacore SPR hVEGFA165 at 25° C. | | | |
|---|---|---|---|
| Compound | $k_{on}$ ($10^6$ 1/Ms) | $k_{off}$ ($10^{-4}$ 1/s) | $K_D$ (pM) |
| Parental VEGFA Ab | 2.93 | 0.39 | 13.2 |
| Compound A | 2.44 | 2.03 | 83.2 |

The values presented in Table 2 are an upper limit for the reported affinity as the off-rate is too slow to accurately quantitate.

TABLE 3

| Biacore SPR hAng2 at 25° C. | | | |
|---|---|---|---|
| Compound | $k_{on}$ ($10^6$ 1/Ms) | $k_{off}$ ($10^{-4}$ 1/s) | $K_D$ (pM) |
| Compound A | 0.24 | 0.32 | 136 |

Affinity Measurement with KinExA KEA

A KinExA 3200 instrument is used to measure binding kinetics to human VEGFA165. Briefly, human VEGFA165 is covalently coupled to NHS-activated sepharose beads (GE Healthcare #17-0906-01) and the binding of free Mab to the conjugated beads is detected on the KinExA 3200. To measure $K_D$, individual tubes containing a fixed concentration (typically 1-5 pM) of the compound are mixed with decreasing concentrations of serially diluted human VEGFA165 and pre-incubated for greater than 24 hours at either 25° C. or 37° C. (depending on the temperature analyzed) in Casein Blocking Buffer (ThermoFisher #37528). Following pre-incubation to reach steady state equilibrium, each sample is subjected to the following five step analysis cycle: 1) a small column of VEGFA165-conjugated beads is packed into a capillary to a predefined height, 2) defined volumes of each discrete human VEGFA165/compound mixture is injected over the column for a defined time period, 3) defined volume of an appropriate fluorescently labeled antibody (I.E. CY5-labeled anti-human Fc gamma specific, Jackson Immunoresearch #309-175-008) is injected over the column, 4) column is washed with 1×PBS to remove excess detection antibody and any non-specifically bound materials and 5) detection of specifically bound materials is measured by excitation and subsequent emission monitoring of the bound secondary antibody. It follows that the relative intensity of signal generated in these steps is proportional to the degree of free/uncomplexed compound present in each solution tested. The resultant composite set of fluorescent intensities is plotted as a function of the concentration of human VEGFA165 present in each discrete sample and fit using the N-curve analysis software (KinExA) to a standard two state binding model to determine $K_D$ for the given MOI. Statistical confidence is reported by calculation of the 95% confidence intervals.

In experiments performed essentially as described, the binding at 37° C. for Compound A was 84 pM (Table 4), and the binding at 25° C. for Compound A was 26.6 pM (Table 5).

TABLE 4

| Kinexa KEA hVEGFA165 at 37° C. | | |
| --- | --- | --- |
| Compound | $K_D$ (pM) | 95% CI Range (pM) |
| Parental VEGFA Ab | 183 | 98.311 |
| Compound A | 84 | 117.50 |

TABLE 5

| Kinexa KEA hVEGFA165 at 25° C. | | |
| --- | --- | --- |
| Compound | $K_D$ (pM) | 95% CI Range (pM) |
| Parental VEGFA Ab | 27 | 14.47 |

Inhibition of Human Ang2 to Human Tie2 Interaction via Solid Phase Elisa

The blocking of human Ang2 binding to its receptor human Tie 2 by a compound of the present invention is measured in a solid phase in vitro ELISA assay. The in vitro cell-based assay is used to establish comparable blocking activity between a compound of the present invention and an Ang2 antibody with the same HCDRs and LCDRs sequences as the scFv polypeptide portion of the compound.

For this assay, high binding 96-well ELISA plates (Costar #2592) are coated with 4 µg/ml (in 100 µl) recombinant human Tie2-Fc (R&D Systems #313-TI), overnight at room temperature. The plates are washed 3× with TBST (Tris buffered saline containing 0.05% Tween 20) and then blocked with 300 µl per well of blocking buffer (0.5% BSA/D-PBS) (BSA: Jackson ImmunoResearch #001-000-162; IgG-free, protease-free) for 1-2 hours at room temperature on an orbital shaker. During the blocking step, in separate polypropylene multiwell plates, 75 µl of 2× test compounds (serially diluted 1:3 in blocking buffer) is added with 75 µl of 2× biotinylated human Ang2 (R&D Systems #BT623) (also diluted in blocking buffer). The compound/biotinylated Ang2 mixtures are then incubated for 1 hour at 37° C. (final biotinylated Ang2 concentration was 100 ng/ml). The blocking solution is removed from the Tie2-Fc coated ELISA plates, after which 50 µl per well of the compound/biotinylated Ang2 mixtures is added (in duplicate wells). The plates are then incubated for 2 hours at room temperature, covered with plate sealers, on an orbital shaker. Plates are then washed 3×, after which 100 µl per well of streptavidin-HRP (R&D Systems #DY998), diluted 1:200 in blocking buffer is added. Plates are then incubated for 35 minutes at room temperature, covered with plate sealers, on an orbital shaker. Plates are then washed again 3×.

Plates are developed by adding 100 µl per well of One Component TMB substrate (Surmodics/BioFX Labs #TMBW-1000-01) which is warmed to room temperature. Development is allowed to progress for 10 minutes at room temperature, plates are covered with aluminum foil. Development is stopped with 100 µl per well of stop solution (Surmodics/BioFX Labs #LSTP-1000-01). Plates are mixed on an orbital shaker after which they are read at 450 nM on an ELISA reader (Molecular Devices SpectraMax 190), using SOFTmax PRO 5.4.1 software (Molecular Devices Corp.). The A450 values reflect the amount of biotinylated Ang2 that remained bound to Tie-2-Fc. Reduction of A450 values reflect blocking of biotinylated Ang2 binding to Tie-2-Fc.

IC50 values for inhibition of Ang2 binding to Tie-2 are calculated with SigmaPlot 9.0, using the "Pharmacology" menu, "Standard Curves Analysis" function. The curve is fit using a 4-parameter logistic fit (Hillslope method).

In experiments performed essentially as described in this assay, Compound A and the Ang2 parental antibody of Compound A result in geometric mean IC50 values (n=1) of 0.118 nM and 0.087 nM respectively. Compound A dose dependently blocks human Ang2 binding to human Tie-2 comparably to the Ang2 parental antibody. This data indicates that the Ang2 scFv polypeptide portion of Compound A has potency in this assay that is comparable to that of the parental Ang2 antibody.

Neutralization of Ang2 Mediated Phosphorylation of Tie2, but not Ang1 Mediated Phosphorylation.

The in vitro cell-based inhibition of human Ang2 by a compound of the present invention is measured in a cell-based assay where Ang1 and Ang2 bind to and induce human Tie2 phosphorylation in a dose-dependent manner. The in vitro cell-based assay is used to evaluate the ability of compounds of the present invention to selectively neutralize Ang2 and not Ang1 mediated phosphorylation of the Tie-2 receptor in a dose-dependent manner. An Ang2 antibody, an Ang2/Ang1 antibody, and a control human IgG4 PAA isotype antibody are included as positive and negative controls, respectively.

The CHO-Tie2 cell line is generated by stable transfection of a full-length human Tie2 receptor (with a 3×FLAG tag at the C-terminus). CHO-Tie2 cells are maintained in complete medium of Hams F-12 (CellGro/Mediatech #10-080-CV), 10% heat inactivated FBS (Life Technologies/Invitrogen #10082-147), 1× antibiotic-antimycotic (Life Technologies/Invitrogen #15240-062), 1.25 mg/ml G418 (Corning Cellgro #30-234-CI), 10 µg/ml puromycin (Calbiochem #540411), and 0.078% sodium bicarbonate (Thermo Hyclone #SH30033.01).

For this assay, CHO-Tie2 cells are resuspended to 10,000 cells per well (in 100 µl growth medium), into the inner 60 wells of poly-lysine coated 96-well plates (BD Biocoat #356640). 200 µl of D-PBS are placed into the edge wells to reduce evaporation. Cells are incubated overnight at 37° C., 95% RH, 5% $CO_2$. The next day, cells are washed once and medium is replaced with 100 µl serum-free growth medium containing 0.1% BSA (Sigma #A7979, low endotoxin). Cells are then starved for 7 to 24 hours in serum-free medium at 37° C., 95% RH, 5% $CO_2$. During the starvation period, compounds (at 6× the final concentrations) are serially diluted 1:2 in polypropylene plates in serum-free growth medium containing 0.1% BSA. Human Ang2 (R&D Systems #623-AN, reconstituted in D-PBS/0.1% BSA) and human Ang1 (R&D Systems #923-AN, reconstituted in D-PBS/0.1% BSA) are also diluted to 6× the final concentration in serum-free growth medium containing 0.1% BSA. Test compounds and the Ang2 or Ang1 ligand are then mixed at a 1:1 ratio (v/v) in polypropylene plates and incubated for 60-80 minutes at 37° C. The compound/ligand mixtures are then added at 50 µl per well to the cells (in triplicate wells per treatment) and incubated for 13 minutes to 21 hours at 37° C., 95% RH, 5% $CO_2$. The final concentration range of compounds are 0.125-383 nM, and the final concentration of human Ang2 and Ang1 is 0.3 µg/ml (approx. 6 nM) and 0.5 µg/ml (approx. 8.9 nM), respectively. After the incubation time, medium is quickly and fully removed from the cells, and cells lysed in 60 µl per well of cold 1× Tris Lysis Buffer (Meso Scale Discovery #R60TX; 150 mM NaCl, 20 mM Tris pH 7.5, 1 mM EDTA, 1 mM EGTA, 1% Triton X-100) which contains freshly added protease and phosphatase inhibitors (1× protease inhibitor cocktail, Sigma #P8340; 1× phosphatase inhibitor cocktail 2, Sigma #P5726; 1× phosphatase inhibitor cocktail 3, Sigma #P0044; 1 mM final activated sodium orthovanadate EMD Chemicals #567540). Plates are then placed on ice for 10 minutes, after which they may be placed on an orbital shaker at low speed for 25 minutes at 4° C. The plates are then sealed and frozen at −80° C.

The day before analysis for phospho-Tie2 (with a human phospho-Tie2 DuoSet ELISA kit from R&D Systems, #DYC2720), high binding ELISA plates (Greiner BioOne, #655081) are coated overnight at 4° C. with 4 µg/ml mouse anti-human total Tie2 capture antibody in 1×ELISA coating buffer (Surmodics/BioFX Labs #COAT-1000-01).

The day of phospho-Tie2 measurement, plates containing lysates are thawed on ice. The coated ELISA plates are washed with wash buffer (1×TBST containing 0.05% Tween 20) and blocked with 300 µl per well of blocking buffer (1% BSA (Jackson ImmunoResearch #001-000-162; IgG-free, protease-free), 0.01% sodium azide) for a minimum of 1 hour at room temperature on an orbital shaker (while covered with plate sealers). During blocking, lysates are diluted 1:5 or 1:10 in polypropylene plates in cold lysis buffer containing protease and phosphatase inhibitors. ELISA plates are washed 4×, and 100 µl per well of diluted lysates or phospho-Tie2 ELISA standards is added and incubated for 2 hours at room temperature, covered with sealers, on an orbital shaker. Plates are washed 4× and 100 µl per well of HRP conjugated mouse anti-phospho tyrosine (diluted as recommended on the vial, in TBST/0.1% BSA) is added. Plates may then be covered with sealers, and incubated for 2 hours at room temperature on an orbital shaker. Plates are then washed 6× and removal of liquid from the wells is ensured. Plates are then developed by adding 100 µl per well of One Component TMB substrate (Surmodics/BioFX Labs #TMBW-1000-01). Plates are allowed to develop for 30 minutes at room temperature covered with aluminum foil. Development is stopped with 100 µl per well of stop solution (Surmodics/BioFX Labs #LSTP-1000-01). Plates are then mixed on an orbital shaker. The ELISA plates are read at 450 nm on an ELISA reader (Molecular Devices SpectraMax 190), using SOFTmax PRO 5.4.1 software (Molecular Devices Corp.). Phospho-Tie2 values for the samples are obtained from the standard curve (4-parameter logistic fit), and multiplied by the dilution factor of 5 or 10.

IC50 values for inhibition of Ang2 induced phospho-Tie2 are calculated with GraphPad Prism 4, using Log-transformed X values. Nonlinear regression (curve fit) analysis (sigmoidal dose response, variable slope) is performed on the log-transformed data to obtain $IC_{50}$ values.

In experiments performed essentially as described in this assay, Compound A dose-dependently neutralizes human Ang2 induced phospho-Tie2 in CHO-Tie2 cells with an IC50 of 0.87 nM (n=1) while the parental Ang2 antibody has an IC50 of 1.01 nM. The results indicate that Compound A neutralizes Ang2 induced phospho-Tie2, but does not neutralize human Ang1 induced phospho-Tie2 in CHO-Tie-2 cells when compared to the positive control Ang2/Ang1 antibody. Moreover, this data indicates that the Ang2 scFv polypeptide portion of Compound A has maintained potency in this assay that is comparable to that of the parental Ang2 antibody.

Neutralization of Human VEGFA Induced Phosphorylation of Human VEGFR2

The in vitro cell-based inhibition of human VEGFA is measured in a cell-based assay where binding of VEGFA165 to VEGFR2 on a VEGFR2 expressing cell line, induces VEGFR2 phosphorylation in a dose-dependent manner. The assay is used to evaluate the ability of a compound of the present invention to selectively neutralize VEGFA mediated phosphorylation of the VEGFR2 receptor in a dose-dependent manner A VEGFA antibody and an irrelevant antibody human IgG4 PAA isotype are included as a positive and negative control, respectively.

For the assay, VEGFR2 expressing human ECFC (endothelial colony forming cells, derived from umbilical cord blood endothelial progenitors) (Endgenitor Technologies, Lot 100506-14-P4, passages 8-10) are seeded at 14,000 cells per well (in 100 µl growth medium), into the inner 60 wells of collagen I coated 96-well plates (BD Biocoat #35-4407) in growth medium: EGM-2MV BulletKit (Lonza #CC-4147). Components of the included EGM-2MV Singlequot bag may be added to 500 ml of EBM-2 basal medium, adjusted to 10% final FBS concentration (Life Technologies/Invitrogen #10082-147, heat inactivated). 250 µl of growth medium are placed into the edge wells to reduce evaporation. Cells are incubated ON at 37° C., 95% RH, 5% $CO_2$. The next day, medium is removed and replaced with 100 µl serum-free EBM-2 basal medium containing 0.1% BSA (Sigma #A7979, low endotoxin). Cells are starved for 6.5 hours at 37° C., 95% RH, 5% $CO_2$. During the starvation period, compounds (at 6× the final concentrations) are serially diluted 1:4 in polypropylene plates in EBM-2/0.1% BSA. Human VEGFA165 is diluted to 6× the final concentration in EBM-2/0.1% BSA. Compounds and VEGFA165 are then mixed at a 1:1 ratio (v/v) in polypropylene plates and incubated for 1 hour at 37° C. The compound/VEGFA165 mixtures are then added at 50 µl per well to the cells (in triplicate wells per treatment) and incubated for 5 minutes at 37° C., 95% RH, 5% $CO_2$. (The final concentration range of compounds is 0.018-300 nM, and the final concentration of human VEGFA165 is 0.16 nM). Medium is removed from the cells, and cells lysed in 60 µl per well of cold 1× Tris Lysis Buffer (Meso Scale Discovery #R60TX; 150 mM NaCl, 20 mM Tris pH 7.5, 1 mM EDTA, 1 mM EGTA, 1% Triton X-100) containing freshly added 1× protease and phosphatase inhibitors (included with the phospho-VEGFR2 assay kit). Plates are placed on ice for 10 minutes, then on an orbital shaker at low speed for 20 minutes at 4° C. Plates are then sealed and frozen at −80° C.

The day of phospho-VEGFR2 measurement, plates containing lysates are thawed on ice. Phospho-VEGFR2 levels are measured using a phospho-VEGFR2 (Tyr1054) whole cell lysate kit, (Meso Scale Discovery #K151DJD). Meso Scale assay plates, pre-coated with an antibody against phospho-VEGFR2, are blocked with 150 µl per well of blocking buffer (3% blocker A in TBST) for a minimum of 1 hour at room temperature on an orbital shaker (while covered with plate sealers). The plates are washed 3× with 1× Meso Scale wash buffer, and 50 µl of lysates is added per well (incubated for 1 hour at room temperature, covered with sealers, on an orbital shaker). The plates are washed 3× and 25 µl per well of 1×MSD SULFO-TAG™ conjugated anti-total VEGFR2 (diluted in the manufacturer's recommended antibody diluent) is added, and incubated for 1 hour at room temperature, covered with sealers, on an orbital shaker. Plates are washed 3× and liquid from the wells is removed. 150 µl per well of 1× Read Buffer T is added to the plates, and read immediately on a Meso Scale Discovery SECTOR Imager MA6000.

IC50 values for inhibition of VEGFA165 induced phospho-VEGFR2 are calculated with GraphPad Prism 4, using Log-transformed X values. Nonlinear regression (curve fit) analysis (sigmoidal dose response, variable slope) are performed on the log-transformed data to obtain IC50 values. If an experiment was performed more than once, the geometric mean IC50 value between experiments is calculated.

In experiments performed essentially as described in this assay, Compound A has an IC50 of 0.252 nM (n=2) that is comparable to the IC50 of 0.194 nM (n=2) for parental VEGFA antibody. The results indicate that the VEGFA antibody portion of Compound A has maintained potency. The results also show that Compound A has comparable VEGFA165 neutralization activity to bevacizumab (purchased from Myoderm Medical Supply, Norristown, Pa.), which has an IC50 of 0.290 nM.

Neutralization of VEGFA Induced Cell Proliferation.

The in vitro cell-based inhibition of human VEGFA by a compound of the present invention is measured in a cell-based assay where VEGFA165 induces proliferation in a dose-dependent manner. The ability of a compound of the present invention to neutralize human VEGFA165 induced proliferation is measured in human ECFC (endothelial colony forming cells, derived from umbilical cord blood endothelial progenitors). VEGFA antibodies and an irrelevant human IgG4 PAA antibody are included as positive and negative controls.

Human ECFC (Endgenitor Technologies, Lot 100506-14-P4) are maintained in collagen coated flasks in EGM-2MV BulletKit (Lonza #CC-4147). Components of the included EGM-2MV Singlequot bag are added to 500 ml of EBM-2 basal medium, adjusted to 10% final FBS concentration (Life Technologies/Invitrogen #10082-147, heat inactivated).

For the assay, ECFC at passages 7-12 is washed twice in pre-warmed cell plating medium, and plated into the inner 60 wells of collagen I coated 96-well plates (BD Biocoat #35-4407) at 4,200 cells per 150 µl/well of cell plating media. 250 µl of assay diluent is added to the edge wells to reduce evaporation. Cell plating medium consists of Medium 199 (M199) with Earle's Salts (Life Technologies/Invitrogen #11150-059) containing 3.3% FBS (Life Technologies/Invitrogen #10082-147, heat inactivated), 10 mM HEPES (Thermo Scientific/HyClone #SH30237.01) and 1× penicillin-streptomycin (Thermo Scientific/HyClone #SV30010). Assay diluent consists of serum-free M199/HEPES/penicillin-streptomycin, containing 0.1% BSA (Sigma #A7979, low endotoxin). Cells are incubated 60-90 minutes at 37° C., 95% RH, 5% $CO_2$ before treating. Compounds and human VEGFA165 are diluted in assay diluent at 8× the final concentrations. Compounds are serially diluted 1:4 in polypropylene plates in assay diluent. Compounds and VEGFA165 are then mixed at a 1:1 ratio (v/v) in polypropylene plates and incubated for 1-3 hours at 37° C. The compound/VEGFA165 mixtures are then added at 50 µl per well to the cells in triplicate wells per treatment and incubated for a total of 3 days at 37° C., 95% RH, 5% $CO_2$. The final concentration range of compounds is 0.049-800 nM, and the final concentration of human VEGFA165 is 0.16-0.5 nM.

Two days before the end of the incubation period, the cells are pulsed with 10 µl (1 µCi) of methyl-$^3$H thymidine (Perkin Elmer #NET027005MC, 6.7 Ci/mmol; 1 mCi/ml stock diluted 1:10 in PBS). At the end of the incubation period, the plates are frozen at −80° C. and then thawed for 1-2 hours at 37° C. The cells are then harvested on 96-well glass fiber filter plates (Perkin Elmer UniFilter, GF/C #6005174) with distilled water. After the filter plates are air dried, the incorporated $^3$H thymidine is counted in 20 µl scintillant per well (MicroScint 0, Perkin Elmer #6013611) on a Perkin Elmer-Packard TopCount microplate scintillation counter.

$IC_{50}$ values for inhibition of VEGFA165 induced proliferation are calculated with GraphPad Prism 4, using Log-transformed X values. Medium alone values are included as the highest point of curves; the X-value (concentration) for medium alone are set to 100× higher than the highest X value. Also, the VEGFA alone values are included as the lowest point of the curves; the concentration for VEGFA alone is set to 100× lower than the lowest X value. Nonlinear regression (curve fit) analysis (sigmoidal dose response, variable slope) is performed on the log-transformed data to obtain IC50 values. If an experiment was performed more than once, the geometric mean IC50 value between experiments is calculated.

In experiments performed essentially as described in this assay, Compound A dose dependently neutralizes human VEGFA165-induced proliferation of ECFC to levels similar to both the parental VEGFA antibody and bevacizumab (n=2-3 experiments) at IC50's of 1.18 nM, 1.38 nM and 2.68 nM, respectively.

Repression of Pathological Angiogenesis in Oxygen-Induced Retinopathy Model.

The in vivo repression of pathological angiogenesis by a VEGFA-Ang2 bispecific molecule, such as Compound A, is measured in a model of oxygen-induced retinopathy in the mouse retina. The assay is used to study the ability of compounds of the present invention to repress pathological angiogenesis in the mouse retina.

For this assay, the day of mouse pup delivery by the pregnant females is marked P0 (postnatal day 0). Following delivery, at day 7 (P7) pups are placed in a chamber at 75% oxygen. At P12, pups are moved back at room air (20% oxygen) and injected with vehicle control (PBS) or 10 mg/kg of Ang2 or VEGFA antibodies or 13.5 mg/kg of the test compound to maintain comparable molar amounts of the molecules. At P15, pups are injected a second time at the same doses. At P17, mice are sacrificed and eyes harvested and fixed in formalin for 5 hours and washed with PBS.

Retinas are then dissected, and stained with anti-CD31 diluted at 1:200 (BD Pharmingen; clone MEC 13.3; #553370), and anti-SMA-FTIC diluted at 1:200 (Sigma; Clone1A4 #F3777). For the anti-CD31 treated retinas, an anti-Rat Alexa-647 antibody diluted at 1:400 (Jackson Immuno Research; #712-606-153) is used as a secondary antibody. Acquisition of the retinas is done by using Nikon Ti, and quantification of area enclosing pathological blood endothelial cell structures, i.e., glomeruloid microvascular proliferation (GMP) of full retina is performed by using FIJI software. High magnification images are acquired using a confocal Nikon Al.

In experiments performed essentially as described in this assay, Compound A and the combination treatment of the parental Ang2 antibody and the parental VEGFA antibody comparably repress GMP area of full retina with a Mean(%) of 17.20% (std error 3.853) and 14.10% (std. error 3.822), respectively, with p=0.9778. Furthermore, Compound A shows increased repression of GMP area of full retina compared to the parental Ang2 antibody or the parental VEGFA antibody treatment alone, which showed a Mean (%) of 83.03% (std error 4.542) p<0.0001 and 40.14% (std. error 2.189) p=0.029, respectively. These results indicate that Compound A has not only maintained function and potency equivalent to the combination treatment of Ang2 antibody plus VEGFA antibody, but also has a superior treatment effect when compared to each agent alone.

TABLE 6

GMP area of full retina

| Parameters | Vehicle | Ang2 parental mAb | VEGFA parental mAb | Ang2 mAb + VEGFA mAb | Compound A |
|---|---|---|---|---|---|
| Mean (%) | 100 | 83.03 | 40.14 | 14.10 | 17.20 |
| Std. Error of Mean | 9.526 | 4.542 | 2.199 | 3.822 | 3.853 |
| P value (Vehicle vs. Compound) (Dunnett's test) | | 0.102 | <0.0001 | <0.0001 | <0.0001 |
| P value (Ang2 mAb vs. Compound) (Dunnett's test) | | | <0.0001 | <0.0001 | <0.0001 |
| P value (VEGFA mAb vs. Compound) (Dunnett's test) | | | | 0.012 | 0.029 |
| P value (Ang2 mAb + VEGFA mAb vs. Compound) (Dunnett's test) | | | | | 0.9778 (non-significant) |

Inhibition of VEGFA Induced Cord Formation

The in vitro inhibition of VEGFA induced cord formation is measured in an in vitro co-culture system. The assay is used to measure inhibition of VEGFA induced cord formation by a compound of the present invention.

For this assay, adipose derived stem cells (ADSC; Lonza #PT5006, lot#OF4505-01) are cultured on Corning culture flasks (Corning #431082) in EGM-2MV medium (Lonza #CC3202). Endothelial colony forming cells (ECFC; Lonza, lot#EGT-ECFC100506r) are cultured on Collagen I coated flasks (BD Biosciences #356486) in EGM-2MV medium supplemented with 5% heat inactivated FBS (Gibco #10082-147). ADSC at passages 4-6 are harvested from culture flasks which are rinsed with DPBS (Hyclone #SH30028.03) followed by TryµLE Express (Gibco #12605-010). ADSC cells are suspended in Basal Medium (MCDC-131 (Gibco #10372-019) supplemented with 10 µg/ml insulin, 1 µM dexamethasone, 30 µg/ml ascorbic acid, 10 µg/ml human transferrin and 50 µg/ml tobramycin). Viable cell count is determined and cells are seeded onto black, clear bottomed 96-well plates (BD Falcon #353219) at $4 \times 10^4$ cells per well in 100 µl Basal Medium. Cells are incubated at 37° C. in 5% $CO_2$ overnight to allow attachment. Next day, ECFC at passages 7-10 is harvested in Basal Medium as above and viable cell count is adjusted to $4 \times 10^4$ cells per ml. Medium is removed from ADSC cells and 100 µl ECFC cell suspension is added to each well. Plates are incubated at 37° C. in 5% $CO_2$ for 2-3 hours to allow cells to settle on top of the ADSC monolayer. Compounds of the present invention are diluted to 80 µg/ml in Basal Medium, and then serially diluted 1:3 with Basal Medium to produce a nine point dose response series. 50 µl of each dilution of compound is added to the co-culture. 50 µl of an 80 ng/ml solution of rhVEGFA (R&D #293-VE/CF, 50 µg/ml in DPBS) prepared in Basal Medium is added to the co-culture plus compound combination. Final concentrations for compounds and rhVEGFA are 20 µg/ml and 20 ng/ml, respectively. Positive control for the assay is 20 ng/ml rhVEGFA in the absence of compound. Negative control for the assay is Basal Medium without rhVEGFA. Plates are then incubated at 37° C. in 5% $CO_2$ for 3 days to allow cords to form.

At the end of the incubation period, medium is aspirated from each well and 100 µl room temperature 80% ethanol is carefully added. Plates are incubated at room temperature for 20 minutes. Ethanol solution is aspirated and wells washed twice with 150 µl DPBS. Anti-huCD31 (R&D #AF806 Affinity purified sheep IgG, 200 ug/ml) and MAB Anti-Actin, alpha-Smooth Muscle-Cy3 (Sigma #C6198) are each diluted 1:250 in 2.5% FBS/DPBS. A 100 µl antibody mixture is added to wells and plates are incubated at 37° C. in 5% $CO_2$ for 2 hours. Plates are then aspirated and wells washed twice with 150 µl DPBS. Alexa Fluor 488 donkey anti-sheep IgG (H+L) (Life Technologies #A11015) is diluted 1:400 and Hoescht 33342 (Life Technologies #H3570) is diluted 1:1000 in 2.5% FBS/DPBS and 100 µl per well is added to plates. Plates are incubated at room temperature protected from light for 30 minutes. Wells are then washed twice with 150 DPBS. 150 µl DPBS is added to each well and plates sealed with black adhesive seals (PerkinElmer #6050173).

Plates are read on the ArrayScan VTI HCS Reader (Cellomics-Thermo Fisher) using the Tube Formation Bio-application. Total Tube Area data is plotted against compound concentrations in nM in GraphPad Prism 6. Compound concentrations are transformed into log data and $IC_{50}$ values for inhibition are calculated by nonlinear regression (sigmoidal dose response, variable slope). Each experiment represents the mean of triplicates and triplicate experiments are expressed as the geometric means and 95% confidence intervals calculated.

In experiments performed essentially as described in this assay, Compound A dose dependently inhibits human VEGFA-induced cord formation in the ADSC/ECFC co-culture system, comparably to bevacizumab and parental VEGFA antibody with mean $IC_{50}$ of 1.680 nM, 1.578 and 1.570 nM, respectively (n=3). This indicates that the VEGFA antibody portion of Compound A has maintained potency that is comparable to the parental VEGFA antibody in this cell based assay.

Compound A Inhibits In Vivo Tumor Growth

The efficacy of the compounds of the present invention is measured via in vivo xenograft models. The antitumor efficacy of the parental VEGFA antibody, Compound A, and its combination is assessed in the subcutaneous triple negative patient derived breast cancer model (EL1997) and the subcutaneous ovarian xenograft model (SKOV3x.1). Mice bearing tumors are treated with compounds diluted in PBS, on a twice weekly basis via intra-peritoneal injection. Tumor growth is determined by three dimensional caliper measurements of tumor volumes twice weekly during the course of treatment.

EL1997 Triple Negative Breast Patient Derived Xenografts:

Immuno-deficient mice bearing EL1997 triple negative breast patient derived xenografts (TNBC PDX) at approximately 350 mm³ volume randomized at n=7 mice/group are treated with vehicle control, parental VEGFA antibody at 20 mg/kg, parental Ang2 antibody at 20 mg/kg, or Antibody A dosed at 26.7 mg/kg. Treatments are administered twice a week for 4 consecutive weeks.

In experiments performed essentially as described, parental VEGFA antibody and parental Ang2 antibody treatment groups exhibits a % T/C (change in tumor volume) of 12% and 56.7%, respectively. Compound A results in a % regression of −15.4% with a p=0.0151 when compared to the parental VEGFA antibody. These results indicate that Compound A has greater efficacy than treatment with either the parental VEGFA antibody or the parental Ang2 antibody alone.

SKOV3x.1 Ovarian Xenografts:

Immuno-deficient mice bearing SKOV3x.1 ovarian xenografts at approximately 250 mm$^3$ volume, randomized at n=10 mice/group, are treated with vehicle control, parental VEGFA antibody at 10 mg/kg, parental Ang2 antibody at 10 mg/kg, combination of parental VEGFA antibody and parental Ang2 antibody at 10 mg/kg each, or 13.3 mg/kg (equimolar to 10 mg/kg of antibody) Compound A. Treatments may be administered twice a week for 4 weeks.

In experiments performed essentially as described, monotherapy treatment of parental VEGFA antibody and of parental Ang2 antibody resulted in a % T/C of 9.6% and 38.5%, respectively. The combination of parental VEGFA antibody and parental Ang2 antibody or Compound A results in tumor regressions of −8.1% and −2.7% respectively. These results indicate in the xenograft model that Compound A has a potential for greater efficacy than parental VEGFA antibody or parental Ang2 antibody alone.

| Amino Acid and Nucleotide Sequences |
|---|
| (HCVR of antibody-Compound A) SEQ ID NO: 1 |
| EVQLLESGGGLVQPGGSLRLSCAASGFTFSSYAMSWVRQAPGKGLEWVS |
| AISGSGGSTYYADSVKGRFTISRDNSKNTLYLQMNSLRAEDTAVYYCAR |
| DPSDSSSWYFAFDIWGQGTTVTVSS |
| (HC of antibody-Compound A) SEQ ID NO: 2 |
| EVQLLESGGGLVQPGGSLRLSCAASGFTFSSYAMSWVRQAPGKGLEWV |
| SAISGSGGSTYYADSVKGRFTISRDNSKNTLYLQMNSLRAEDTAVYYC |
| ARDPSDSSSWYFAFDIWGQGTTVTVSSASTKGPSVFPLAPCSRSTSES |
| TAALGCLVKDYFPEPVTVSWNSGALTSGVHTFPAVLQSSGLYSLSSVV |
| TVPSSSLGTKTYTCNVDHKPSNTKVDKRVESKYGPPCPPCPAPEAAGG |
| PSVFLFPPKPKDTLMISRTPEVTCVVVDVSQEDPEVQFNWYVDGVEVH |
| NAKTKPREEQFNSTYRVVSVLTVLHQDWLNGKEYKCKVSNKGLPSSIE |
| KTISKAKGQPREPQVYTLPPSQEEMTKNQVSLTCLVKGFYPSDIAVEW |
| ESNGQPENNYKTTPPVLDSDGSFFLYSRLTVDKSRWQEGNVFSCSVMH |
| EALHNHYTQKSLSLSLG |
| (HC of antibody/linker/scFv polypeptide-Compound A) SEQ ID NO: 3 |
| EVQLLESGGGLVQPGGSLRLSCAASGFTFSSYAMSWVRQAPGKGLEWV |
| SAISGSGGSTYYADSVKGRFTISRDNSKNTLYLQMNSLRAEDTAVYYC |
| ARDPSDSSSWYFAFDIWGQGTTVTVSSASTKGPSVFPLAPCSRSTSES |
| TAALGCLVKDYFPEPVTVSWNSGALTSGVHTFPAVLQSSGLYSLSSVV |
| TVPSSSLGTKTYTCNVDHKPSNTKVDKRVESKYGPPCPPCPAPEAAGG |
| PSVFLFPPKPKDTLMISRTPEVTCVVVDVSQEDPEVQFNWYVDGVEVH |
| NAKTKPREEQFNSTYRVVSVLTVLHQDWLNGKEYKCKVSNKGLPSSIE |
| KTISKAKGQPREPQVYTLPPSQEEMTKNQVSLTCLVKGFYPSDIAVEW |
| ESNGQPENNYKTTPPVLDSDGSFFLYSRLTVDKSRWQEGNVFSCSVMH |
| EALHNHYTQKSLSLSLGGGGSGGGGSGGGGSQVQLVQSGAEVKKPGAS |
| VKVSCKASGYSFTDYNMVWVRQAPGQCLEWMGYIDPYNGGTGYNQKFE |
| GRVTMTTDTSTSTAYMELRSLRSDDTAVYYCARTRDRYDVWYFDVWGQ |
| GTLVTVSSGGGGSGGGGSGGGGSGGGGSGGGGSDIQMTQSPSSVSASV |
| GDRVTITCKASQDVYIAVAWYQQKPGKAPKLLIYWASTRDTGVPSRFS |
| GSGSGTDFTLTISSLQPEDFATYYCHQYSSYPPTFGCGTKVEIK |
| (LCVR of antibody-Compound A) SEQ ID NO: 4 |
| DIVMTQSPATLSVSPGQRATLSCRASQNIRNNLAWYQQKRGQAPRLLI |
| YGASTRATGIPDRFSGSGSGADFTLTISKLEPEDFAVYYCQQYGSSPR |
| TFGQGTKVDIK |
| (LC of antibody-Compound A) SEQ ID NO: 5 |
| DIVMTQSPATLSVSPGQRATLSCRASQNIRNNLAWYQQKRGQAPRLLI |
| YGASTRATGIPDRFSGSGSGADFTLTISKLEPEDFAVYYCQQYGSSPR |
| TFGQGTKVDIKRTVAAPSVFIFPPSDEQLKSGTASVVCLLNNFYPREA |
| KVQWKVDNALQSGNSQESVTEQDSKDSTYSLSSTLTLSKADYEKHKVY |
| ACEVTHQGLSSPVTKSFNRGEC |
| (scFv polypeptide-Compound A) SEQ ID NO: 6 |
| QVQLVQSGAEVKKPGASVKVSCKASGYSFTDYNMVWVRQAPGQCLEWM |
| GYIDPYNGGTGYNQKFEGRVTMTTDTSTSTAYMELRSLRSDDTAVYYC |
| ARTRDRYDVWYFDVWGQGTLVTVSSGGGGSGGGGSGGGGSGGGGSGGG |
| GSDIQMTQSPSSVSASVGDRVTITCKASQDVYIAVAWYQQKPGKAPKL |
| LIYWASTRDTGVPSRFSGSGSGTDFTLTISSLQPEDFATYYCHQYSSY |
| PPTFGCGTKVEIK |
| (HCVR of scFv polypeptide-Compound A) SEQ ID NO: 7 |
| QVQLVQSGAEVKKPGASVKVSCKASGYSFTDYNMVWVRQAPGQCLEWM |
| GYIDPYNGGTGYNQKFEGRVTMTTDTSTSTAYMELRSLRSDDTAVYYC |
| ARTRDRYDVWYFDVWGQGTLVTVSS |
| (LCVR of scFv polypeptide-Compound A) SEQ ID NO: 8 |
| DIQMTQSPSSVSASVGDRVTITCKASQDVYIAVAWYQQKPGKAPKLLIY |
| WASTRDTGVPSRFSGSGSGTDFTLTISSLQPEDFATYYCHQYSSYPPTF |
| GCGTKVEIK |
| (DNA of HC of antibody/linker/scFv polypeptide-Compound A) SEQ ID NO: 9 |
| GAGGTGCAGCTGTTGGAGTCTGGGGGAGGCTTGGTACAGCCTGGGGGGTC |
| CCTGAGACTCTCCTGTGCAGCCTCTGGATTCACCTTTAGCAGCTATGCCA |
| TGAGCTGGGTCCGCCAGGCTCCAGGGAAGGGGCTGGAGTGGGTCTCAGCT |
| ATTAGTGGTAGTGGTGGTAGCACATACTACGCAGACTCCGTGAAGGGCCG |
| GTTCACCATCTCCAGAGACAATTCCAAGAACACGCTGTATCTGCAAATGA |
| ACAGCCTGAGAGCCGAGGACACGGCCGTATATTACTGTGCAAGAGATCCC |

| Amino Acid and Nucleotide Sequences |
|---|
| TCGGATAGCAGCAGCTGGTACTTTGCTTTTGATATCTGGGGCCAAGGGAC |
| CACGGTCACCGTCTCCTCAGCCTCTACCAAGGGCCCATCGGTCTTCCCGC |
| TAGCGCCCTGCTCCAGGAGCACCTCCGAGAGCACAGCCGCCCTGGGCTGC |
| CTGGTCAAGGACTACTTCCCCGAACCGGTGACGGTGTCGTGGAACTCAGG |
| CGCCCTGACCAGCGGCGTGCACACCTTCCCGGCTGTCCTACAGTCCTCAG |
| GACTCTACTCCCTCAGCAGCGTGGTGACCGTGCCCTCCAGCAGCTTGGGC |
| ACGAAGACCTACACCTGCAACGTAGATCACAAGCCCAGCAACACCAAGGT |
| GGACAAGAGAGTTGAGTCCAAATATGGTCCCCCATGCCCACCCTGCCCAG |
| CACCTGAGGCCGCCGGGGGACCATCAGTCTTCCTGTTCCCCCCAAAACCC |
| AAGGACACTCTCATGATCTCCCGGACCCCTGAGGTCACGTGCGTGGTGGT |
| GGACGTGAGCCAGGAAGACCCCGAGGTCCAGTTCAACTGGTACGTGGATG |
| GCGTGGAGGTGCATAATGCCAAGACAAAGCCGCGGGAGGAGCAGTTCAAC |
| AGCACGTACCGTGTGGTCAGCGTCCTCACCGTCCTGCACCAGGACTGGCT |
| GAACGGCAAGGAGTACAAGTGCAAGGTCTCCAACAAAGGCCTCCCGTCCT |
| CCATCGAGAAAACCATCTCCAAAGCCAAAGGGCAGCCCCGAGAGCCACAG |
| GTGTACACCCTGCCCCCATCCCAGGAGGAGATGACCAAGAACCAGGTCAG |
| CCTGACCTGCCTGGTCAAAGGCTTCTACCCCAGCGACATCGCCGTGGAGT |
| GGGAAAGCAATGGGCAGCCGGAGAACAACTACAAGACCACGCCTCCCGTG |
| CTGGACTCCGACGGCTCCTTCTTCCTCTACAGCAGGCTAACCGTGGACAA |
| GAGCAGGTGGCAGGAGGGGAATGTCTTCTCATGCTCCGTGATGCATGAGG |
| CTCTGCACAACCACTACACACAGAAGAGCCTCTCCCTGTCTCTGGGTGGC |
| GGAGGCTCCGGGGGAGGGGTAGCGGAGGAGGGGGATCCCAGGTTCAGCT |
| GGTGCAGTCTGGAGCTGAGGTGAAGAAGCCTGGGGCCTCAGTGAAGGTCT |
| CCTGCAAGGCTTCTGGTTACTCATTCACTGACTACAACATGGTGTGGGTG |
| CGACAGGCCCCTGGACAATGCCTTGAGTGGATGGGATATATTGATCCTTA |
| CAATGGTGGTACTGGCTACAACCAGAAGTTCGAGGGCAGAGTCACCATGA |
| CCACAGACACATCCACGAGCACAGCCTACATGGAGCTGAGGAGCCTGAGA |
| TCTGACGACACGGCCGTGTATTACTGTGCGAGAACGAGGGATAGGTACGA |
| CGTCTGGTACTTCGATGTCTGGGGCCAGGGAACCCTGGTCACCGTCTCCT |
| CAGGAGGCGGAGGTTCCGGGGGAGGGGGCAGCGGAGGAGGCGGATCGGGC |
| GGAGGAGGAAGTGGAGGCGGAGGATCTGACATCCAGATGACCCAGTCTCC |
| ATCTTCCGTGTCTGCATCTGTAGGAGACAGAGTCACCATCACTTGTAAGG |
| CCAGTCAGGATGTGTATATTGCTGTAGCCTGGTATCAGCAGAAACCAGGG |
| AAAGCCCCTAAGCTCCTGATCTATTGGGCATCCACCCGGGACACTGGGGT |
| CCCATCAAGGTTCAGCGGCAGTGGATCTGGGACAGATTTCACTCTCACCA |
| TCAGCAGCCTGCAGCCTGAAGATTTTGCAACTTACTATTGTCACCAATAT |
| AGCAGCTATCCTCCTACGTTCGGCTGCGGGACCAAGGTGGAGATCAAA |

| Amino Acid and Nucleotide Sequences |
|---|
| (DNA of LC of antibody-Compound A) SEQ ID NO: 10 |
| GATATTGTGATGACTCAGTCTCCAGCCACCCTGTCTGTGTCTCCAGGGCA |
| AAGAGCCACCCTCTCCTGCAGGGCCAGTCAAAATATTAGGAATAACTTAG |
| CCTGGTACCAGCAGAAACGTGGCCAGGCTCCCAGGCTCCTCATCTATGGT |
| GCGTCCACTCGGGCCACAGGTATCCCAGACAGGTTCAGTGGCAGTGGGTC |
| TGGGGCGGACTTCACTCTCACCATCAGCAAACTGGAGCCTGAAGATTTTG |
| CAGTTTATTACTGTCAGCAATATGGTAGCTCACCTCGGACGTTCGGCCAA |
| GGGACCAAAGTGGATATCAAAAGAACTGTGGCGGCGCCATCTGTCTTCAT |
| CTTCCCGCCATCTGATGAGCAGTTGAAATCCGGAACTGCCTCTGTTGTGT |
| GCCTGCTGAATAACTTCTATCCCAGAGAGGCCAAAGTACAGTGGAAGGTG |
| GATAACGCCCTCCAATCGGGTAACTCCCAGGAGAGTGTCACAGAGCAGGA |
| CAGCAAGGACAGCACCTACAGCCTCAGCAGCACCCTGACGCTGAGCAAAG |
| CAGACTACGAGAAACACAAAGTCTACGCCTGCGAAGTCACCCATCAGGGC |
| CTGAGCTCGCCCGTCACAAAGAGCTTCAACAGGGGAGAGTGC |
| (human VEGFA165) SEQ ID NO: 11 |
| APMAEGGGQNHHEVVKFMDVYQRSYCHPIETLVDIFQEYPDEIEYIFKPS |
| CVPLMRCGGCCNDEGLECVPTEESNITMQIMRIKPHQGQHIGEMSFLQHN |
| KCECRPKKDRARQENPCGPCSERRKHLFVQDPQTCKCSCKNTDSRCKARQ |
| LELNERTCRCDKPRR |
| (human Ang2) SEQ ID NO: 12 |
| YNNFRKSMDSIGKKQYQVQHGSCSYTFLLPEMDNCRSSSSPYVSNAVQRD |
| APLEYDDSVQRLQVLENIMENNTQWLMKLENYIQDNMKKEMVEIQQNAVQ |
| NQTAVMIEIGTNLLNQTAEQTRKLTDVEAQVLNQTTRLELQLLEHSLSTN |
| KLEKQILDQTSEINKLQDKNSFLEKKVLAMEDKHIIQLQSIKEEKDQLQV |
| LVSKQNSIIEELEKKIVTATVNNSVLQKQQHDLMETVNNLLTMMSTSNSA |
| KDPTVAKEEQISFRDCAEVFKSGHTTNGIYTLTFPNSTEEIKAYCDMEAG |
| GGGWTIIQRREDGSVDFQRTWKEYKVGFGNPSGEYWLGNEFVSQLTNQQR |
| YVLKIHLKDWEGNEAYSLYEHFYLSSEELNYRIHLKGLTGTAGKISSISQ |
| PGNDFSTKDGDNDKCICKCSQMLTGGWWFDACGPSNLNGMYYPQRQNTNK |
| FNGIKWYYWKGSGYSLKATTMMIRPADF |
| SEQ ID NO: 13 GGGGSGGGGS |
| SEQ ID NO: 14 GGGGSGGGGSGGGGS |
| SEQ ID NO: 15 GGGGSGGGGSGGGGSGGGGS |
| SEQ ID NO: 16 GGGGSGGGGSGGGGSGGGGSGGGGS |
| SEQ ID NO: 17 GGGSGGGGSGGGGS |

We claim:

1. A compound, comprising an antibody fused by two linkers to two single chain fragment variable (scFv) polypeptides, wherein: a) the antibody comprises two identical heavy chains (HCs) and two identical light chains (LCs), wherein each HC comprises a heavy chain variable region (HCVR) comprising SEQ ID NO: 1, and wherein each LC comprises a light chain variable region (LCVR) comprising SEQ ID NO: 4, b) the two scFv polypeptides are identical and each comprise an HCVR operably linked to an LCVR, wherein each HCVR has the amino acid sequence of SEQ ID NO: 7, and wherein each LCVR has the amino acid sequence of SEQ ID NO: 8, and c) the two linkers are identical glycine-rich linkers that each operably link the carboxy-terminus of one HC of the antibody to the amino-terminus of one of the scFv polypeptides.

2. The compound of claim 1, wherein the two scFv polypeptides each comprise the carboxy-terminus of the HCVR of one scFv polypeptide operably linked to the amino-terminus of the LCVR of one scFv polypeptide.

3. The compound of claim 1, wherein the antibody comprises two heavy chains (HCs) and two light chains (LCs), wherein each HC has the amino acid sequence of SEQ ID NO: 2, and each LC has the amino acid sequence of SEQ ID NO: 5.

4. The compound of claim 3, wherein each scFv polypeptide has the identical amino acid sequence of SEQ ID NO: 6.

5. A compound comprising two first polypeptides and two second polypeptides wherein each of the first polypeptides has the amino acid sequence of SEQ ID NO: 3, and each of the second polypeptides has the amino acid sequence of SEQ ID NO: 5.

6. The compound of claim 5, wherein each of the first polypeptides forms an inter-chain disulfide bond with each of the second polypeptides, and the first polypeptide forms two inter-chain disulfide bonds with the other first polypeptide, and each of the first polypeptides forms seven intra-chain disulfide bonds.

7. A mammalian cell comprising a DNA molecule comprising a polynucleotide sequence encoding a first polypeptide comprising the amino acid sequence of SEQ ID NO: 3 and a polynucleotide sequence encoding a second polypeptide comprising the amino acid sequence of SEQ ID NO: 5, wherein the cell is capable of expressing a compound comprising the first polypeptide and the second polypeptide.

8. A process for producing a compound comprising two first polypeptides comprising SEQ ID NO: 3 and two second polypeptides comprising SEQ ID NO: 5, comprising cultivating the mammalian cell of claim 7 under conditions such that the compound is expressed, and recovering the expressed compound.

9. A compound obtainable by the process of claim 8.

10. A pharmaceutical composition, comprising the compound of claim 1, and an acceptable carrier, diluent, or excipient.

11. A method of treating cancer, comprising administering to a patient in need thereof, an effective amount of the compound of claim 1.

12. The method of claim 11, wherein the cancer is breast cancer, lung cancer, ovarian cancer, gastric cancer, colorectal cancer, or hepatocellular carcinoma.

13. A method of treating proliferative retinopathy, comprising administering to a patient in need thereof, an effective amount of the compound of claim 1.

14. The method of claim 13, wherein the proliferative retinopathy is diabetic retinopathy, or retinopathy of prematurity.

15. A method of treating angiogenic eye disease, comprising administering to a patient in need thereof, an effective amount of the compound of claim 1.

16. The method of claim 15, wherein the angiogenic eye disease is neovascular glaucoma, age-related macular degeneration, diabetic macular edema, corneal neovascularization, conical graft neovascularization, conical graft rejection, retinal/choroidal neovascularization, neovascularization of the angle (rubeosis), ocular neovascular disease, vascular restenosis, or arteriovenous malformations (AVM).

* * * * *

UNITED STATES PATENT AND TRADEMARK OFFICE
CERTIFICATE OF CORRECTION

PATENT NO. : 9,932,397 B2  
APPLICATION NO. : 15/005042  
DATED : April 3, 2018  
INVENTOR(S) : Donmienne Doen Mun Leung et al.

Page 1 of 1

It is certified that error appears in the above-identified patent and that said Letters Patent is hereby corrected as shown below:

On the Title Page

Column 2 (Other Publications), Line 26, please delete "2213-22773" and insert --2213-2223--, therefor.

Signed and Sealed this  
Fifth Day of June, 2018

Andrei Iancu  
*Director of the United States Patent and Trademark Office*